United States Patent
Doty et al.

(10) Patent No.: US 8,641,710 B2
(45) Date of Patent: Feb. 4, 2014

(54) MAGNETICALLY COUPLING DEVICES FOR MAPPING AND/OR ABLATING

(75) Inventors: John Richard Doty, Sandy, UT (US); Thomas Jared Bunch, South Jordan, UT (US); Troy J. Orr, Draper, UT (US)

(73) Assignee: Intermountain Invention Management, LLC, Salt Lake City, UT (US)

( * ) Notice: Subject to any disclaimer, the term of this patent is extended or adjusted under 35 U.S.C. 154(b) by 24 days.

(21) Appl. No.: 13/356,622

(22) Filed: Jan. 23, 2012

(65) Prior Publication Data

US 2012/0239021 A1    Sep. 20, 2012

Related U.S. Application Data

(63) Continuation-in-part of application No. 11/938,700, filed on Nov. 12, 2007, now Pat. No. 8,100,899.

(51) Int. Cl.
*A61B 18/14* (2006.01)

(52) U.S. Cl.
USPC .......................................................... 606/41

(58) Field of Classification Search
USPC ............... 606/32–50; 607/101–105, 115–116
See application file for complete search history.

(56) References Cited

U.S. PATENT DOCUMENTS

| | | | |
|---|---|---|---|
| 4,004,298 A | | 1/1977 | Freed |
| 5,429,131 A | * | 7/1995 | Scheinman et al. .......... 600/374 |
| 5,617,854 A | * | 4/1997 | Munsif ......................... 600/374 |
| 5,720,775 A | * | 2/1998 | Larnard .......................... 607/122 |
| 5,885,278 A | * | 3/1999 | Fleischman ..................... 606/41 |
| 5,897,553 A | * | 4/1999 | Mulier et al. ................... 606/41 |
| 5,911,720 A | * | 6/1999 | Bourne et al. .................. 606/41 |
| 6,099,542 A | * | 8/2000 | Cohn et al. ..................... 606/167 |
| 6,292,678 B1 | * | 9/2001 | Hall et al. ...................... 600/374 |
| 6,314,963 B1 | | 11/2001 | Vaska et al. |
| 6,527,767 B2 | | 3/2003 | Wang et al. |
| 6,871,085 B2 | * | 3/2005 | Sommer ........................ 600/374 |
| 6,899,710 B2 | | 5/2005 | Hooven |
| 6,932,811 B2 | | 8/2005 | Hooven et al. |
| 6,974,454 B2 | | 12/2005 | Hooven |
| 7,008,418 B2 | | 3/2006 | Hall et al. |
| 7,113,831 B2 | | 9/2006 | Hooven |

(Continued)

FOREIGN PATENT DOCUMENTS

| EP | 1 880 687 | 1/2008 |
|---|---|---|
| EP | 1 943 973 | 4/2010 |

(Continued)

OTHER PUBLICATIONS

Gillinov et al., "Atrial Fibrillation: Current Surgical Options and Their Assessment", *Ann Thorac Surg*, vol. 74, pp. 2210-2217, 2002.

(Continued)

*Primary Examiner* — Michael Peffley
*Assistant Examiner* — Daniel Fowler
(74) *Attorney, Agent, or Firm* — Stoel Rives LLP

(57) ABSTRACT

Systems for ablating tissue can include a pair of electrode assemblies. The electrode assemblies can automatically align on opposing sides of operative tissue due to magnetic interaction. One assembly can move automatically in response to the other assembly due to the magnetic interaction. Some systems are capable of cooling the electrode assemblies during ablation procedures.

32 Claims, 13 Drawing Sheets

(56) References Cited

U.S. PATENT DOCUMENTS

| | | | |
|---|---|---|---|
| 7,211,082 | B2 | 5/2007 | Hall et al |
| D544,602 | S | 6/2007 | Hughett, Sr. et al. |
| 7,229,469 | B1 | 6/2007 | Witzel et al. |
| 7,288,092 | B2 | 10/2007 | Hooven |
| 7,291,161 | B2 | 11/2007 | Hooven |
| 7,487,780 | B2 | 2/2009 | Hooven |
| 7,530,980 | B2 | 5/2009 | Hooven |
| 7,582,086 | B2 | 9/2009 | Privitera et al. |
| 7,618,435 | B2 * | 11/2009 | Opolski .................. 606/213 |
| 7,799,025 | B2 | 9/2010 | Wellman |
| 7,938,828 | B2 | 5/2011 | Koblish |
| 8,048,072 | B2 | 11/2011 | Verin et al. |
| 8,100,899 | B2 | 1/2012 | Doty et al. |
| 8,100,900 | B2 | 1/2012 | Prinz et al. |
| 8,221,415 | B2 | 7/2012 | Fancischelli |
| 8,430,875 | B2 | 4/2013 | Ibrahim et al. |
| 2005/0187545 | A1 * | 8/2005 | Hooven et al. ............. 606/41 |
| 2005/0203561 | A1 | 9/2005 | Palmer et al. |
| 2005/0203562 | A1 | 9/2005 | Palmer et al. |
| 2006/0069385 | A1 | 3/2006 | Lafontaine et al. |
| 2006/0106375 | A1 | 5/2006 | Werneth et al. |
| 2006/0149121 | A1 | 7/2006 | Hughett et al. |
| 2006/0161147 | A1 | 7/2006 | Privitera et al. |
| 2006/0161149 | A1 | 7/2006 | Privitera et al. |
| 2006/0161151 | A1 | 7/2006 | Privitera et al. |
| 2006/0167478 | A1 | 7/2006 | Miller et al. |
| 2007/0185477 | A1 | 8/2007 | Hooven |
| 2007/0191826 | A1 | 8/2007 | Park et al. |
| 2007/0270799 | A1 | 11/2007 | Fancischelli |
| 2008/0009853 | A1 | 1/2008 | Martin et al. |
| 2008/0114350 | A1 | 5/2008 | Park et al. |
| 2008/0172048 | A1 | 7/2008 | Martin et al. |
| 2008/0243141 | A1 | 10/2008 | Privitera et al. |
| 2008/0275446 | A1 | 11/2008 | Messerly |
| 2008/0294154 | A1 | 11/2008 | Ibrahim et al. |
| 2008/0319440 | A1 | 12/2008 | Richardson et al. |
| 2009/0012545 | A1 | 1/2009 | Williamson, IV et al. |
| 2009/0124847 | A1 | 5/2009 | Doty et al. |
| 2009/0163905 | A1 | 6/2009 | Winkler et al. |
| 2010/0004661 | A1 * | 1/2010 | Verin et al. ............ 606/129 |
| 2011/0060331 | A1 | 3/2011 | Ibrahim et al. |
| 2011/0066000 | A1 | 3/2011 | Ibrahim et al. |
| 2011/0282250 | A1 | 11/2011 | Fung et al. |
| 2012/0083664 | A1 | 4/2012 | Bertolero et al. |
| 2012/0172872 | A1 | 7/2012 | Nollert et al. |

FOREIGN PATENT DOCUMENTS

| | | |
|---|---|---|
| WO | WO 00/69353 | 11/2000 |
| WO | WO 01/80724 | 11/2001 |
| WO | WO 03/037162 | 5/2003 |
| WO | WO 2004/074854 | 9/2004 |
| WO | WO 2004/093659 | 11/2004 |
| WO | WO 2005/081868 | 9/2005 |
| WO | WO 2005/104972 | 11/2005 |
| WO | WO 2005/110205 | 11/2005 |
| WO | WO 2006/055166 | 5/2006 |
| WO | WO 2006/073582 | 7/2006 |
| WO | WO 2007/100754 | 9/2007 |
| WO | WO 2008/010039 | 1/2008 |
| WO | WO 2009/064761 | 5/2009 |
| WO | WO 2011/065983 | 6/2011 |
| WO | WO 2011/129893 | 10/2011 |
| WO | WO 2012/065177 | 5/2012 |
| WO | WO 2013/013098 | 1/2013 |
| WO | WO 2013/013099 | 1/2013 |
| WO | WO 2013/112584 | 8/2013 |

OTHER PUBLICATIONS

Benussi et al., "Surgical Ablation of Atrial Fibrillation with a Novel Bipolar Radiofrequency Device", *J Thorac Cardiovasc Surg*, vol. 130, No. 2, pp. 491-497, Aug. 2005.

Wolf et al., "Video-assisted Bilateral Pulmonary Vein Isolation and Left Atrial Appendage Exclusion for Atrial Fibrillation", *J Thorac Cardiovasc Surg*, vol. 130, No. 3, pp. 797-802, Sep. 2005.

Doty et al., Comparison of Standard Maze III and Radiofrequency Maze Operations for Treatment of Atrial Fibrillation, *J Thorac Cardiovasc Surg*, vol. 133, No. 4, pp. 1037-1044, Apr. 2007.

"RF Ablation" www.bostonscientific.com, 2 pages, Aug. 14, 2007.

Saltman, Adam E. "Completely Endoscopic Microwave Ablation of Atrial Fibrillation on the Beating Heart Using Bilateral Thoracoscopy", www.ctsnet.org, 10 pages, Sep. 4, 2007.

Maze procedure www.wikipedia.org, 5 pages, Sep. 9, 2007.

International Search Report issued on Oct. 7, 2009 in International Application No. PCT/US2008/083193 (published as WO 2009/064761).

Written Opinion of the International Searching Authority issued on Oct. 7, 2009 in International Application No. PCT/US2008/083193 (published as WO 2009/064761).

International Preliminary Report on Patentability issued on May 18, 2010 in International Application No. PCT/US2008/083193 (published as WO 2009/064761).

International Search Report issued on Apr. 1, 2013 in International Application No. PCT/US2013/022746 (published as WO 2013/112584).

Written Opinion of the International Searching Authority issued on Apr. 1, 2013 in International Application No. PCT/US2013/022746 (published as WO 2013/112584).

Office Action dated Aug. 23, 2012 in U.S. Appl. No. 12/781,072, (filed May 17, 2010; issued as U.S. Patent No. 8,430,875 on Apr. 30, 2013).

Amendment dated Nov. 14, 2012 in U.S. Appl. No. 12/781,072, (filed May 17, 2010; issued as U.S. Patent No. 8,430,875 on Apr. 30, 2013).

Notice of Allowance dated Jan. 3, 2013 in U.S. Appl. No. 12/781,072, (filed May 17, 2010; issued as U.S. Patent No. 8,430,875 on Apr. 30, 2013).

Listings of References Cited in U.S. Appl. No. 12/781,072, (filed May 17, 2010; issued as U.S. Patent No. 8,430,875 on Apr. 30, 2013).

* cited by examiner

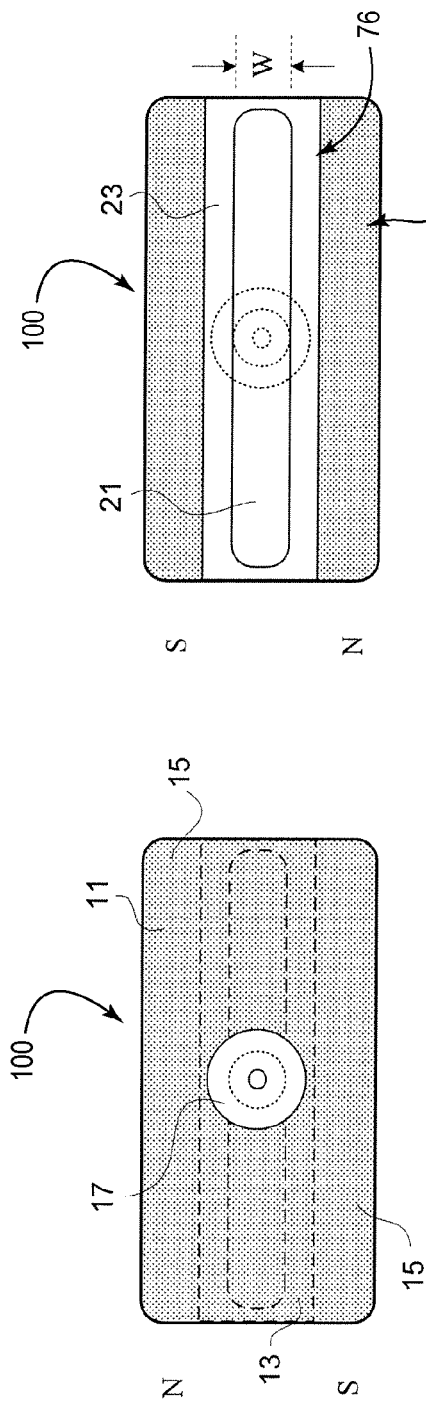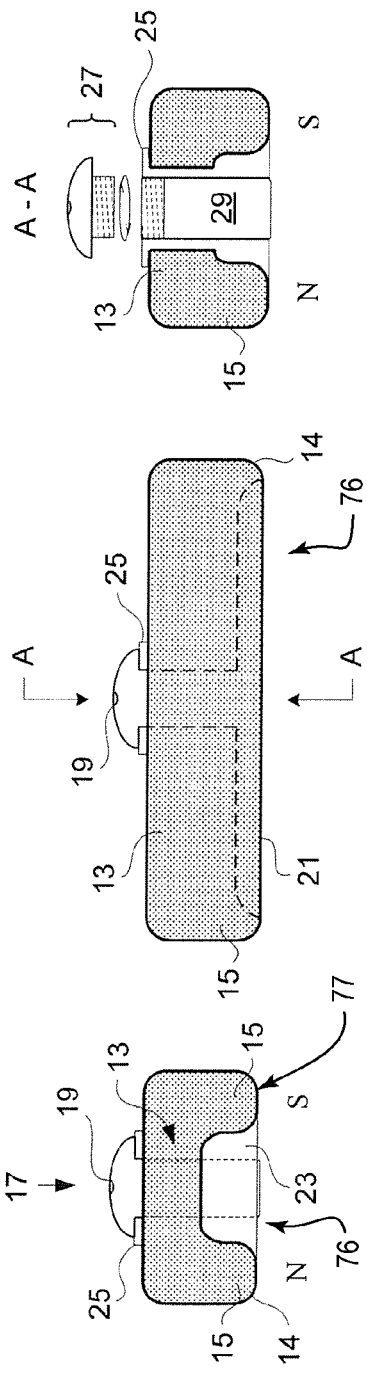

MAGNETICALLY COUPLING DEVICES FOR MAPPING AND/OR ABLATING

CROSS-REFERENCE TO RELATED APPLICATIONS

This application is a continuation-in-part of prior U.S. patent application Ser. No. 11/938,700, filed Nov. 12, 2007, titled COMBINED ENDOCARDIAL AND EPICARDIAL MAGNETICALLY COUPLED ABLATION DEVICE, which issued as U.S. Pat. No. 8,100,899 on Jan. 24, 2012, the entire contents of which are hereby incorporated by reference herein.

BACKGROUND

1. Technical Field

The present disclosure relates generally to surgical ablation. More specifically, the disclosure relates to a system in which bipolar electrodes for radiofrequency ablation are aligned.

2. Description of Related Art

Atrial fibrillation ("AF") is a heart disease that affects one to two percent of the population of the United States. It has been estimated that at any given time, about 2 million people in the United States experience some form of AF, and about 160,000 new cases are diagnosed annually. The prevalence of AF and the health risks associated with it increase with age.

In a patient with AF, the electrical impulses that are normally generated by the sinoatrial node are overwhelmed by disorganized electrical activity in the atrial tissue, leading to an irregular conduction of impulses to the ventricles that generate the heartbeat. The result is an irregular heartbeat, which may be intermittent or continuous. In human populations, AF-induced irregular heartbeat is a significant source of stroke, heart failure, disability, and death.

There are a number of surgical options available for treating AF. One approach pioneered by Dr. James Cox and associates was first performed in 1987, and after several refinements, has evolved into what is now widely known as the Cox-Maze III procedure. In this procedure, the left atrial appendage is excised, and a series of incisions and/or cryolesions are arranged in a maze-like pattern in the atria. The incisions encircle and isolate the pulmonary veins. The resulting scars block the abnormal electrical pathways, improving normal signal transmission and restoring regular heart rhythm. While the success rate is relatively good, the Cox-Maze III and variations thereof are complex open-heart surgeries, requiring cardiopulmonary bypass, median sternotomy, and endocardial incisions that require suturing of the atria. The risk of complications from Cox-Maze III remains significant.

More recently, less invasive techniques have been proposed that use heating or cooling sources to create impulse-blocking lesions on the heart by ablation rather than incision. For example, a procedure known as microwave minimaze, which may be performed epicardially, uses microwave energy to destroy electrical pathways in the atria by heating the tissue at the resonant frequency of the water molecule. In this procedure, small incisions are made on each side of the chest for inserting surgical tools and an endoscope. A flexible microwave antenna is moved along guide catheters into position behind the heart and energized. Aided by the endoscope, the surgeon guides the antenna along the atria to create the pattern of lesions around the pulmonary veins. Clinical research indicates that microwave ablation has a relatively high success rate of about 80%, and allows for the creation of transmural rather than superficial scars. However, the resonance effect of the microwave can be difficult to control, resulting in variable scar formation, and can cause unwanted damage to surrounding tissue.

Other ablation techniques have been developed that use a combination of incisions, cryoablation, and unipolar or bipolar radiofrequency ("RF") energy to create the pattern of lesions achieved in the original Cox-Maze III procedure. The cryoablation technique per se has seen limited use due to the rigidity of the cryoprobes and to the technical difficulties inherent in the procedure. Unipolar systems have been used successfully in epicardial procedures on a beating heart. However, the transmural lesions created using a unipolar electrode are difficult to control due to the composition of the diseased atrial wall and to the effects of convective cooling from blood flow through the atria. The unipolar RF technique has also been used for ablation in endocardial procedures with somewhat elevated risk factors. Endocardial ablation has been associated with unwanted perforation of surrounding organs, due mainly to the difficulty of achieving consistent burn penetration.

Whether epicardial or endocardial, the unipolar procedure is inherently challenging because it can involve a surgeon moving the electrode from point to point and effectively connect the dots to create a desired burn path. If the electrode is moved too slowly, prolonging the burn time at any one point, excessive tissue may be destroyed. If the electrode is moved too quickly along the burn path, or if it is inaccurately placed, gaps may occur in the lesion scar and the abnormal electrical pathways that cause AF may not be completely interrupted. In the latter case, a surgeon may repeat the maze procedure one or more times, thereby multiplying the risk factors. In about half of all cases, a surgeon might repeat the ablation procedure one or more times to achieve the desired results.

Bipolar RF ablation is becoming more common. It is effective in creating transmural scars and among all procedures has the best current success rate of about 80% to 90% for treating AF. Many problems, however, can arise from this procedure and lead to further complications. The electrodes used for bipolar ablation are typically clamps, which can be placed on the inside or outside of the atrium to burn a lesion into the clamped area of tissue. Use of the clamp on the inside atrial wall, however, can involve opening the atrium to accommodate the clamp. The use of two point electrodes in a bipolar procedure can be impractical for transmural ablation, as the surgeon would need to effect simultaneous placement of an endocardial and an epicardial probe, and maintain precise control over the speed and placement of the electrodes. If the placement pattern is inaccurate, an excessive amount of atrial tissue may lie within the burn path, and result in unnecessary destruction of tissue.

Some of the more serious complications that can arise from any of the foregoing ablation procedures are those caused by time-dependent deep heating through excessive heat transfer. A perforation of the atrial wall due to excessive heating can cause permanent structural damage to the heart, or to the heart and to surrounding tissue. In one scenario, a perforation of the heart can cause a pericardial effusion or cardiac tamponade, which can be fatal without immediate evacuation of the pericardial cavity and corrective surgery. In another scenario, excessive heat transmitted by RF energy or microwaves can permeate the thin wall of the left atrium and fuse it with the esophagus, forming a fistula between the two organs. This creates a pathway into the heart for bacteria from the esophagus, posing a significant risk of infection, endocarditis, systemic sepsis, and mediastinitus outside the heart and in the heart itself. Excessive burning can also injure the endothelium, causing a blood clot that can embolize and lodge in another blood vessel or in the brain and cause a stroke or heart attack.

More recently, to minimize the risk of esophageal injury from excessive heat transfer, complex safety precautions are employed in conjunction with unipolar RF ablation. These include the use of proton pump inhibitors, fluid hydration, esophageal mapping, imaging, temperature monitoring, and energy delivery optimization. To optimize energy delivery, lesions are created by applying higher power over a shorter time period to the ablation site. For example, one technique employs a point electrode mounted in an irrigated catheter tip. The electrode is energized with a continuous RF current to deliver about 50 Watts to the ablation site, and the catheter is dragged across the atrial wall for a duration of about 2-5 seconds. The short duration minimizes the risk of time dependent deep heating. However, the surgeon might pass the electrode along the same lesion path multiple times to achieve a desired result, potentially waiting about two minutes between each pass. This undesirably prolongs the procedure.

SUMMARY

Improvement of the efficacy of surgical and interventional vascular treatment for AF may result from a more reliable and/or less invasive means for controlling the RF energy during ablation of the atrial tissue. One or more embodiments discussed herein can ameliorate or eliminate one or more of the drawbacks discussed above.

Certain embodiments can provide a minimally invasive means for aligning bipolar electrodes on opposing sides of operative tissue to improve the reliability of RF ablation. In some embodiments, the device includes a set of first and second complementary magnetic electrode assemblies. Each electrode assembly includes a magnetic member and an electrical conductor; in some embodiments, the magnetic member also functions as an electrical conductor. When positioned on opposing sides of tissue, such as an atrial wall, the complementary magnetic electrode assemblies automatically align their respective electrical conductors through magnetic attraction, and, thus positioned, the electrical conductors can complete an electrical circuit. Each electrode assembly may be mechanically coupled to a positioning device, such as an intravenous or percutaneous catheter, and each may include means for attaching a transmission wire through the positioning device to the electrical conductor.

In some embodiments, the magnetic member of an electrode assembly comprises a permanent magnet, which may be formed as a U-shaped trough from iron or other magnetic material. The U-shaped trough has a cross-member connecting two substantially parallel legs, with a north pole occurring on one end of the U and a south pole occurring on the other end of the U. The electrical conductor passes through the trough in a direction parallel to the legs of the U. Along the contacting surface of the electrode assembly, the electrical conductor connects to a transmitting element that may form an elongated conductive segment running midway between and parallel to the ends of the U. The magnetic coupling surface provides a smooth tissue contacting surface to facilitate translation and positioning of the assembly along the surface of the operative tissue by means of an intracorporeal positioning device that is mechanically linked to the assembly.

In other embodiments, each complementary electrode assembly has a substantially cylindrical bar magnet with north and south poles at opposite ends of a longitudinal axis. An electrical conductor is mechanically coupled to and electrically insulated from the cylindrical magnet. The electrical conductor has a wire receiving terminal on one surface and a transmitting element on a tissue contacting surface. The transmitting element may form an elongated conductive segment that is substantially parallel to the longitudinal axis. A mechanical linkage couples the assembly to an intracorporeal positioning device. Bearings may be provided to allow one or both of the cylindrical bar magnets to rotate with respect to the electrical conductor so that a surgeon can position the electrode to a desired location by rolling it along the surface of the operative tissue.

In various embodiments, when complementary electrodes are positioned on opposite sides of the operative tissue, magnetic forces align the north pole of one assembly opposite the south pole of the other assembly, causing the transmitting elements to properly align on opposite sides of the tissue. In some embodiments, one assembly includes a permanent magnet, whereas another assembly includes an unmagnetized magnetic material that is attracted by the permanent magnet and is aligned therewith. In an ablation procedure, the alignment allows transmission of RF current between the electrodes for burning a lesion into the tissue along a line having a length corresponding to the length of the transmitting elements. In some embodiments, one electrode may be linked to a rigid positioning device while the complementary electrode may be linked to a flexible positioning device, so that when only the rigidly linked electrode is manipulated by a surgeon, the flexibly linked electrode automatically tracks the rigidly linked electrode to maintain dynamic alignment. In some embodiments, the set of electrode assemblies includes an endocardial electrode having a rigid positioning device and an epicardial electrode having a flexible positioning device. In other embodiments, the set of electrode assemblies includes an epicardial electrode having a rigid positioning device and an endocardial electrode having a flexible positioning device.

Some embodiments include a steering catheter, which may be used in positioning an electrode assembly. Other or further embodiments include cooling systems that are configured to cool one or more of the electrodes.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1 is a top view of an embodiment of a magnetic electrode assembly for performing RF ablation, wherein a magnetic core forms a slideable U-shaped trough.

FIG. 2 is a bottom view of the magnetic electrode assembly of FIG. 1.

FIG. 3 is an end view of the magnetic electrode assembly of FIG. 1.

FIG. 4 is a side view of the magnetic electrode assembly of FIG. 1.

FIG. 5 is a cross-sectional side view of the magnetic electrode assembly of FIG. 1 taken along section A-A in FIG. 4.

DETAILED DESCRIPTION

Figure 7:
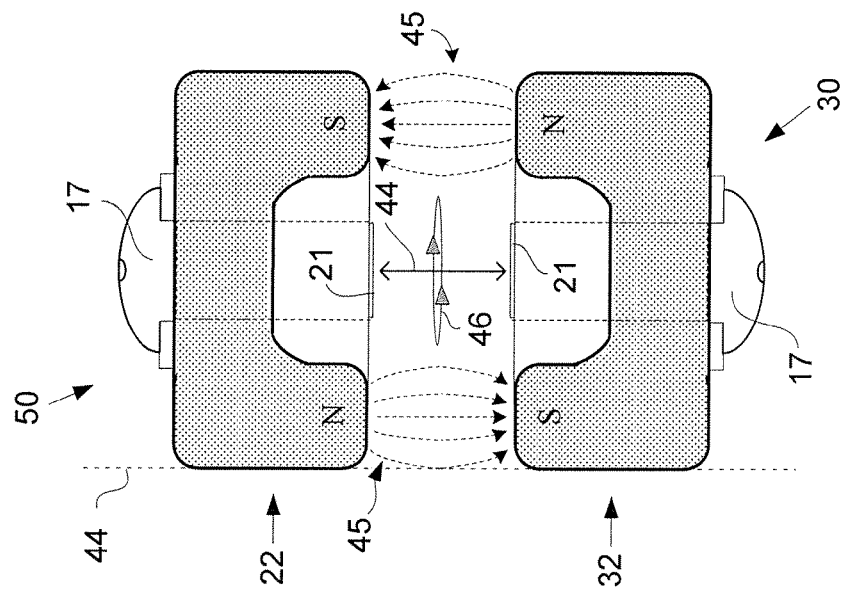
FIG. 7 is a magnified side view of the device of FIG. 6, showing the direction of magnetic flux lines of the permanent magnets with respect to the direction of magnetic flux lines created by current flow in central conductors.

The following disclosure presents various embodiments for providing automatically aligning bipolar electrodes on opposing sides of operative tissue. Certain embodiments can improve precision and efficacy of transmural ablation in the treatment of AF, and thus this particular context is discussed, although the embodiments are not necessarily limited to any specific procedure or context. The apparatus and methods disclosed herein may be applied to any surgical procedure that can benefit from precision alignment of two or more transmitting elements across a tissue mass, such as for the purpose of scoping, suturing, burning, cutting, freezing, excising, electrically mapping, or otherwise treating or interacting with the tissue. Applications of various embodiments include, but are not limited to, endometrial ablation, tumor ablation, treatment of WPW syndrome, observation or measurement of electrical properties of tissue, and placement of catheters, pacemakers, imaging devices, biosensors, and prostheses.

Certain devices can include a set of first and second complementary magnetic electrode assemblies. In some devices, each magnetic electrode assembly includes a magnetic core mechanically coupled to and electrically insulated from an electrical conductor. At least one of the magnetic cores may be a permanent magnet, while the magnetic core of the complementary assembly may be a permanent magnet or a demagnetized (e.g., unmagnetized) material, such as, for example, a ferromagnetic material in which magnetic domains are unaligned. When positioned on opposing sides of tissue such as an atrial wall, the complementary magnetic electrodes automatically align their respective electrical conductors as a result of magnetic attraction to complete an electrical circuit. Each assembly may be mechanically coupled to a positioning device, such as an intravenous or percutaneous catheter, and each may include means for attaching a transmission wire through the positioning device to the electrical conductor. Certain embodiments can enable a surgeon to manipulate just one of the magnetic electrode assemblies, as movement thereof urges the complementary electrode into automatic alignment, and in some instances, subsequent tracking thereof, through magnetic attraction.

Throughout the disclosure, directional terms such as, for example, "top" and "bottom," are used to describe the relative location of parts as viewed by a reader observing the drawings. These terms are used for illustrative purposes only, and are not intended to place limitations on the orientation of any part. Terms such as "right atrium" and "left atrium" are used in their customary sense to indicate specific heart chambers viewed from the perspective of the patient.

FIG. 1 shows a top view of one embodiment of a magnetic electrode assembly 100 for performing RF ablation. In this embodiment, electrode assembly 100 includes a magnetic core 11, which may also be referred to as a magnetic member or as a magnetically interactive member, in the form of a slideable U-shaped trough with a cross member portion 13 connecting two substantially parallel leg sections 15. The end of one leg 15 corresponds to the north magnetic pole N and the end of the other leg 15 corresponds to the south magnetic pole S. Magnetic core 11 may be formed from any magnetic material, such as, for example, iron, cobalt, nickel, ceramic composite, alnico, lanthanoid, samarium-cobalt, neodymium-iron-boron, ticonal, or rare earth materials, or any combination thereof, by any suitable technique such as casting, molding, sintering, stacking, etc. The magnetic core 11 can comprise a permanent magnet, such as a permanent magnet formed of any of the foregoing materials. Assembly 100 can be further understood with reference to the bottom view of FIG. 2, the end view of FIG. 3, the side view of FIG. 4, and the cross-sectional end view of FIG. 5.

As further discussed below, in some embodiments, the magnetic member 11 of one magnetic electrode assembly 100 can be complementary to the magnetic member 11 of another magnetic electrode assembly 100, and the complementary magnetic electrode assemblies 100 can function together as an ablation system. The complementary assemblies 100 can interact with one another across the wall of an anatomical structure, such as the heart. In some embodiments, the magnetic member 11 of each magnetic electrode assembly 100 comprises a permanent magnet, such as described above, such that the magnetic members 11 exhibit mutual magnetic attraction to each other. In other embodiments, one of the magnetic members 11 comprises a permanent magnet, whereas the other magnetic member 11 comprises a magnetically influenced material, such that the permanent magnet attracts the magnetically influenced material.

The terms "magnetic member" and "magnetically interactive member" are used herein in a broad sense, and can include both "magnetic sources" and "magnetically influenced materials." The term "magnetic source" includes any suitable object or system that provides a magnetic field, such as, for example a permanent magnet, an electromagnet, or any other suitable magnetic device. The term "permanent magnet" is used herein in its ordinary sense, and includes any suitable material that provides a magnetic field in the absence of application of a magnetic field thereto, or stated otherwise, that independently or intrinsically provides a magnetic field. However, the term "permanent magnet" does not necessarily imply that the material has always provided a magnetic field or will always provide a magnetic field, since, for example, the material may have been magnetized at some prior time (e.g., via an alignment of magnetic domains), or may be demagnetized at some later time (e.g., by heating the material past its Curie temperature or via some form of degradation in which magnetic domains transition to an unaligned state). The term "magnetically influenced material" includes materials that are capable of magnetization but are not magnetized (e.g., do not independently produce a magnetic field), or that are otherwise capable of reacting to (e.g., being attracted by) or otherwise being influenced by a magnetic field. For example, magnetically influenced materials can include demagnetized, or unmagnetized, ferromagnetic and/or ferrimagnetic materials.

Assembly 100 further includes an electrical conductor 17 that is bonded to and electrically insulated from magnetic core 11. Conductor 17 may be formed from any conductive material such as copper, aluminum, steel, silver, gold, etc. In the embodiment shown, conductor 17 penetrates magnetic core 11 through cross-member 13. Conductor 17 includes a wire receiving terminal 19 on the top side of the assembly, and a transmitting element 21 on the bottom side of the assembly. Wire receiving terminal 19 may be a soldering point, soldering post, male connector, female connector, plug, socket, crimp site, or other means for terminating a wire or other conductive element to conductor 17.

The bottom side of electrode assembly 100 is also referred to herein as the tissue contacting surface 76. At the tissue contacting surface 76, conductor 17 forms transmitting element 21. In the embodiment shown, transmitting element 21 forms an elongated conductive segment that is exposed along the tissue contacting surface and lies in a direction parallel to a magnetic coupling surface 77. In other embodiments, the elongated conductive segment may lie in a direction not parallel to the magnetic coupling surface 77, or may have some degree of curvature, depending on the application. The width W of the transmitting element may be on the order of about 1 mm or less. As the transmitting element 21 is drawn along a tissue wall, it may be energized to deliver electrical current through the atrial tissue until, or so that, a burn scar develops wherever element 21 contacts the tissue. After one or more passes, the resulting burn scar may be made wide enough to interrupt abnormal electrical pathways in the atrium in the same way that an excision scar interrupts those pathways in a conventional maze procedure. Conversely, the width W can be sufficiently narrow to prevent unnecessary or undesired damage to the tissue. With the electrode assembly 100 energized in a fixed position against operative tissue, an elongated conductive transmitting element 21 can create a linear ablation without the surgeon having to move the assembly from point to point.

In the illustrated embodiment, an insulator 23 provides electrical insulation between magnetic core 11 and conductor 17. Insulator 23 may be any biocompatible dielectric material suitable for this purpose. In the embodiment shown, insulator 23 includes a flanged end 25 to insulate the top surface of magnetic core 11 from a top portion of conductor 17 that contains the wire receiving terminal 19. The remainder of insulator 23 may be formed or molded for compression fit within the volume between magnetic core 11 and conductor 17, as shown. In one embodiment, conductor 17 may be formed from two mating parts to facilitate assembly—a top portion 27 and a lower portion 29. For example, electrode assembly 100 may be assembled by compression-fitting insulator 23 against the inside of magnetic core 11 by inserting the lower portion of conductor 17 upward into the core. The top portion 27 of conductor 17 may then be installed by threaded engagement with the lower portion 29, as illustrated in the cross-sectional view of FIG. 5.

In one embodiment, the length of magnetic core 11 may be on the order of about 5 to 10 mm, with a pole thickness of about 3 to 5 mm. Other dimensional values and design constraints for magnetic core 11 are possible, and may vary according to the particular application. For example, in an application for transmural RF ablation of an atrium, the design basis for magnetic core 11 can ensure that the core is moveable along the surface of an atrial wall having an average thickness between about 3 mm and about 5 mm, and that a complementary pair of magnetic cores positioned on opposite sides of the atrial wall generates sufficient magnetic force to urge the pair into symmetrical alignment. To facilitate movement along a surface of operative tissue such as an atrial wall, magnetic core 11 may be formed with one or more rounded corners 14, and may also be formed with a smooth surface at any point that may come into contact with tissue.

Figure 6:
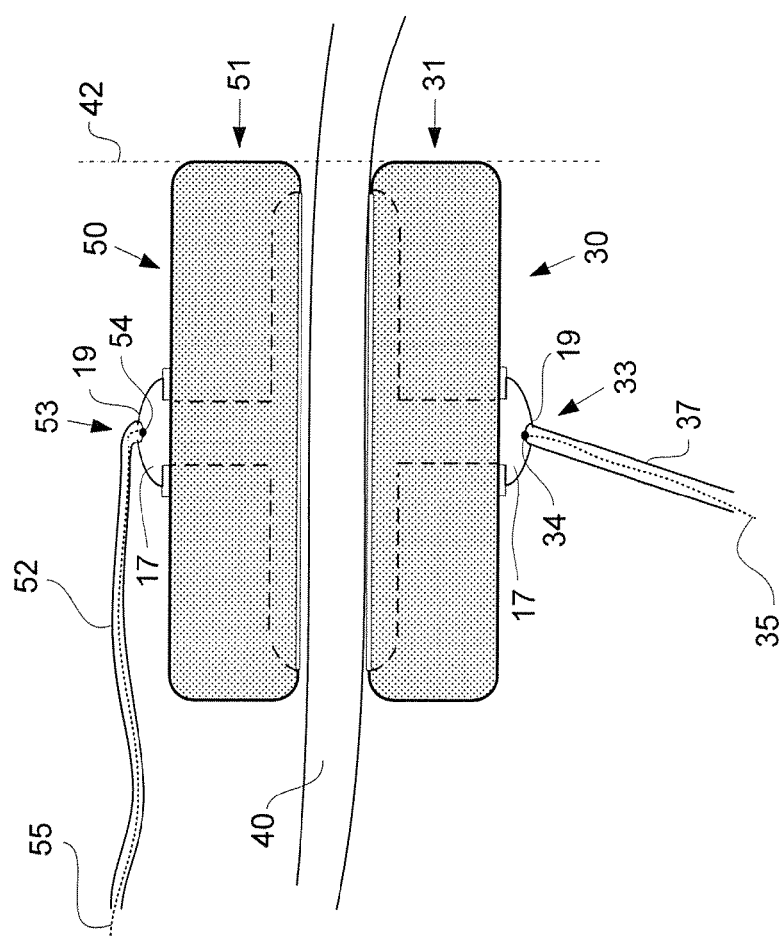
FIG. 6 is a side view of a magnetically coupled device having U-shaped magnets positioned for transmural ablation of an atrium, wherein an endocardial electrode is shown contacting the atrial wall and aligned with and facing an epicardial electrode that is contacting an opposite side of the atrial wall.

FIG. 6 illustrates a magnetically coupled device positioned for transmural ablation of an atrium. The device consists of two complementary magnetic electrode assemblies 30, 50 each having U-shaped magnetic core. Preferably, each electrode assembly 30, 50 has a construction similar to electrode assembly 100. Alternatively, one electrode assembly may include a magnetic core that is a permanent magnet, while the complementary electrode assembly may include a magnetic core that is a demagnetized (or unmagnetized) magnetic material, or stated otherwise, the complementary magnetic core may comprise a magnetically influenced material. In FIG. 6, an endocardial electrode assembly 30 is shown contacting an atrial wall 40 and facing an epicardial electrode assembly 50 that is contacting an opposite side of the atrial wall. FIG. 7 shows a magnified side view of the same magnetically coupled device. The orientation of the electrode assemblies in FIGS. 6 and 7 is an example of an optimal alignment for transmission.

In the optimal alignment for transmission depicted in FIGS. 6 and 7, sides 31 and 51 of the cores lie substantially in the same plane 42. Similarly, sides 22 and 32 lie substantially in the same plane 44. In their respective figures, planes 42 and 44 are normal to the page, and each is indicated by a straight line. With electrode assemblies 30 and 50 in optimal alignment, transmitting elements 21 face each other across the atrial wall with a minimal volume of tissue between them.

Optimal alignment thus also corresponds to the orientation that provides a minimum electrical resistance between electrodes along any segment of the atrial wall.

With reference again to FIG. 6, mechanical linkage of the electrode assemblies 30 and 50 to intracorporeal positioning devices are now described. The mechanical linkage may be either rigid or flexible. Various embodiments are possible in which both linkages may be rigid, in which both linkages may be flexible, or in which one linkage may be rigid and the other linkage may be flexible. In the embodiment shown in FIG. 6, linkage 37 is a rigid linkage connected to endocardial electrode assembly 30, and linkage 52 is a flexible linkage connected to epicardial electrode 50.

Linkage 37 may be a solid rod or hollow tube formed from biocompatible plastic or metal suitable for intravenous or subcutaneous use, similar to that used in the construction of catheters. Linkage 37 can be, for example, a rigid positioning device such as a catheter with a remotely positionable end. In one embodiment, linkage 37 may be an arm extending from conductor 17 and connectable to a subcutaneous probe or an intravenous catheter. Preferably, linkage 37 is hollow or includes one or more lumens so as to allow one or more wires 35 to pass within the linkage and connect electrically to conductor 17. The distal end 33 of linkage 37 may connect mechanically to conductor 17 at or around wire receiving terminal 19 by welding, adhesion, or other fastening means. Wire 35 may connect to conductor 17 at a connection or soldering point 34 at wire receiving terminal 19. Other connection arrangements are also possible. For example, distal end 33 of linkage 37 may connect directly to the magnetic core, or to a plate or bracket (not shown) fixed elsewhere on the surface of electrode assembly 30. In another embodiment, wire 35 may run through a separate lumen in linkage 37, or may run externally to the mechanical linkage. It is also noted that the wire 35 may comprise any suitable electrical lead or electrically conducting member. For example, in some embodiments, the wire or lead 35 may comprise a guide wire and/or a flexible tube capable of conducting charge.

Whatever the arrangement, mechanical linkage 37 allows a surgeon to manipulate the position of electrode assembly 30 within the atrium or other intracorporeal location. When moved into an approximate desired location, e.g. within the atrium near the pulmonary veins, linkage 37 allows the surgeon to translate electrode assembly 30 along the atrial wall while maintaining contact therewith to finely adjust its position. In one embodiment, the linkage-to-electrode interface may include a mechanism such as a ball joint (not shown) to allow adjustment of electrode position with respect to the linkage with three degrees of freedom. It is also contemplated that the positioning of the electrode assembly may be accomplished with the aid of a video imaging device such as an endoscope introduced through a subxiphoid port.

Linkage 52 is illustrated as a flexible rod or flexible hollow tube formed from biocompatible plastic or metal suitable for intravenous or subcutaneous use. In one embodiment, linkage 52 may be a flexible extension connectable to a subcutaneous probe or an intravenous catheter with sufficient slack to avoid undue constrainment of the electrode assembly, and to provide three degrees of freedom for movement of electrode position with respect to the linkage. Linkage 52 can be hollow, or include one or more lumens, so as to allow one or more wires 55 to pass within the linkage and connect electrically to conductor 17. For example, linkage 52 may comprise a layer of biocompatible insulation, such as teflon, that surrounds conductor 17. The distal end 53 of linkage 52 may connect mechanically to conductor 17 at or around wire receiving terminal 19 by welding, adhesion, or other fastening means. Wire 55 may connect to conductor 17 at a connection or soldering point 54 at wire receiving terminal 19. Other connection mechanical and electrical connections are possible, as discussed in the context of linkage 37.

The flexible characteristic of linkage 52 combined with the mutual magnetic attraction between electrode cores allows electrode assembly 50 to automatically position itself into optimal alignment on the outer atrial wall (or other intracorporeal location) without direct manipulation by a surgeon. When manually introduced to an approximate desired location, e.g., on the outer atrial wall near the pulmonary veins, linkage 52 tracks the movement of its complementary electrode assembly while maintaining contact with the operative tissue. In this manner, an ablation device may optimally align opposing bipolar electrodes automatically, thereby maintaining dynamic alignment of the electrical conductors and improving the precision of ablation. Moreover, certain embodiments may give the surgeon the ability to align bipolar electrodes with one hand, thereby reducing the complexity of the procedure and advantageously freeing the other hand to manipulate some other surgical instrument or device.

Figure 14:
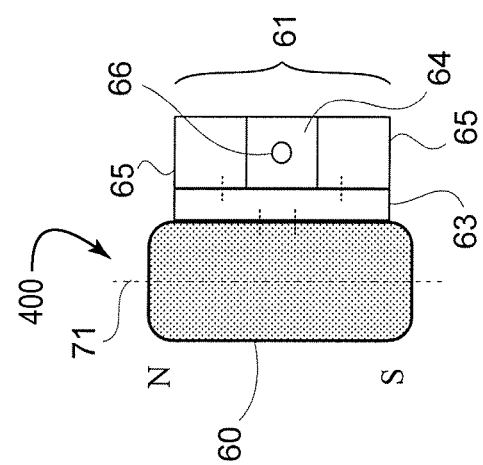
FIG. 14 is a top view of another embodiment of a magnetic electrode assembly for performing RF ablation, wherein an elongated transmitting element lies parallel to a slideable bar magnet.

Turning now to FIG. 7, the electrical and magnetic interactions between the illustrated electrode assemblies 30 and 50 are described. In optimal alignment, the magnetic flux lines 45 of the magnetic cores pass from the north poles N to the south poles S in the directions shown, and the mutual magnetic force acts in the same general directions to pull the transmitting elements 21 into close proximity on opposite sides of the operative tissue. During an ablation procedure, wires 35 and 55 are connected to opposite electrical terminals of an RF generator 90 (FIG. 14). With electrode assemblies 30 and 50 in optimal alignment, the RF circuit is completed through the operative tissue. In this example, the operative tissue includes the portion of atrial wall 40 that borders transmitting elements 21. As the electric current is applied, adjacent ions within the tissue begin to oscillate at the same frequency as the RF current. These ions experience opposing frictional forces, and the resulting thermal energy elevates the ambient temperature around the transmitting elements causing coagulation necrosis and cellular damage at temperatures between about 50° C. and about 100° C.

Typically, the RF current needed to damage heart tissue at these temperatures is sustained for a duration of about 60 seconds in the range of about 500 mA to about 1 A, rms. This current oscillates in conductors 17 at about 500 MHz in the directions indicated by the double-arrow line 44, creating magnetic flux lines 46. The electrode assemblies are configured so that magnetic flux resulting from the flow of electrons will lie in planes normal to flux lines 45. This helps to ensure that magnetic flux 46 will have negligible effect on the magnetic forces acting to maintain the electrodes in optimal alignment. In some embodiments, the strength of the magnetic field created by the complementary cores will dominate any additional magnetic effects introduced by the RF current or by a DC component superimposed on the RF current. Temperatures, currents, and/or frequencies other than those recited above are also possible.

Other configurations of a magnetic core for an electrode assembly are possible. For example, in another embodiment, the magnetic core 11 may form a V-shaped trough, with two legs extending from a central notch at a separation angle of about 90 degrees. In such as embodiment, electrical conductor 17 may pass through the central notch area. Additional embodiments are disclosed in the following paragraphs.

Figure 8:
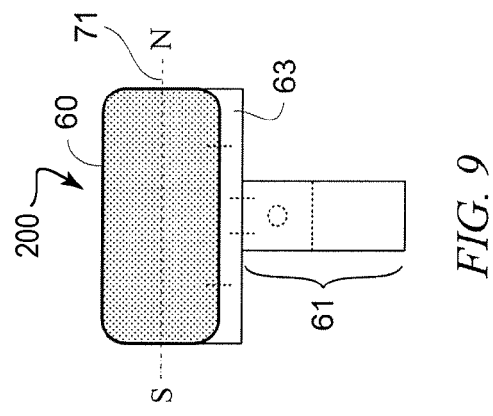
FIG. 8 is a top view of another embodiment of a magnetic electrode assembly for performing RF ablation, wherein the magnetic core forms a slideable cylindrical bar magnet.

FIG. 8 is a top view of an embodiment of a magnetic electrode assembly 200 for performing RF ablation. In assembly 200, the magnetic core 60 forms a slideable cylindrical bar magnet have a north pole N and a south pole S, as indicated, and a longitudinal axis 71 therebetween. The outer surface of magnetic core 60 is preferably smooth throughout. An electrical conductor 61 is bonded (or mechanically coupled) to and electrically insulated from core 60, and may extend in a direction generally perpendicular to the longitudinal axis 71 of the cylindrical bar magnet. The mechanical coupling may be effected in any suitable manner. In assembly 200, core 60 is shown mechanically coupled to conductor 61 by one or more fasteners 62, which may be studs, pins, rivets, or threaded screws. A firm dielectric material 63 may be used to insulate conductor 61 from core 60. One or more additional fasteners 62 may be used to connect the insulation 63 to conductor 61. The magnetic, conductive, and dielectric materials of assembly 200 may be selected from stock similar to that disclosed above for electrode assembly 100.

Figure 9:
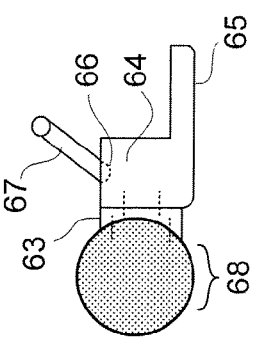
FIG. 9 is a bottom view of the magnetic electrode assembly of FIG. 8.
Figure 10:
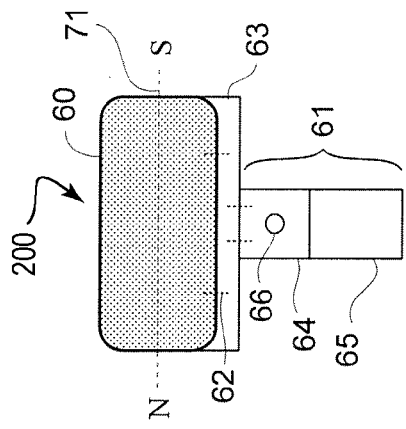
FIG. 10 is an end view of the magnetic electrode assembly of FIG. 8.
Figure 11:
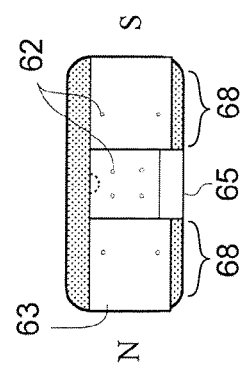
FIG. 11 is a side view of the magnetic electrode assembly of FIG. 8.

Assembly 200 can be further understood with reference to the bottom view of FIG. 9, the end view of FIG. 10, and the side view of FIG. 11. Electrical conductor 61 may further include a wire receiving terminal 64 and a transmitting element 65. Wire receiving terminal 64 may provide a post, a planar area, or a recessed area for soldering a wire to conductor 61, or a male or female connection for coupling to a complementary plug or receptacle. In the embodiment shown, wire receiving terminal 64 provides a recessed area 66 for wire connection. In one embodiment, conductor 61 may be cast or machined as a single metal part.

The bottom edge of the cylindrical core 60 forms a magnetically coupling surface 68 for magnetically coupling to a complementary core. At all times during movement of coupling surface 68, the transmitting element 65 remains adjacent and in fixed relation to coupling surface 68. A rigid mechanical linkage 67 is provided at the top of conductor 61 to link assembly 200 to an intracorporeal positioning means capable of guiding or sliding the coupling surface 68 along a surface of operative tissue. In a complementary electrode assembly, rigid mechanical linkage 67 may be replaced with a flexible mechanical linkage 69.

Figure 12:
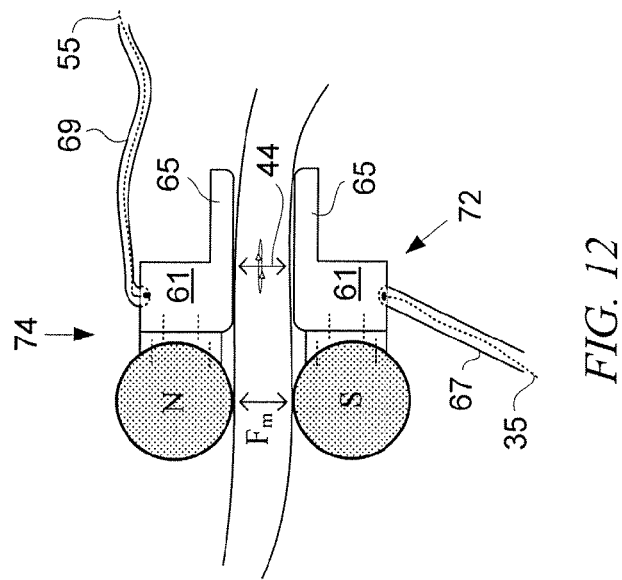
FIG. 12 is a side view of a magnetically coupled device having cylindrical bar magnets positioned for transmural ablation of an atrium, wherein an endocardial electrode is shown contacting the atrial wall and aligned with and facing an epicardial electrode that is contacting an opposite side of the atrial wall.

FIG. 12 illustrates a side view of a magnetically coupled device having cylindrical bar magnets in optimal position for transmural ablation of an atrium. The device consists of a complementary pair of slideable electrode assemblies 72, 74 similar in construction to assembly 200. An endocardial electrode assembly 72 is shown contacting an atrial wall 40 and aligned with and facing an epicardial electrode assembly 74 that is contacting an opposite side of the atrial wall. As previously described, the device is in optimal position for transmural ablation when assembly 72 is directly opposite assembly 74 so that transmitting elements 65 can create a linear ablation in the tissue when energized.

In this embodiment, the alternating electric field 44 is offset from the area of greatest magnetic force, $F_m$, lying directly between the magnetic cores. This offset, combined with the dominant strength of the magnetic field created by the complementary cores renders negligible any additional magnetic effects introduced by RF or DC current flowing through conductors 61. Otherwise, the operating principles of the device of FIG. 12 are similar to the device of FIG. 7. During translation of electrode assembly 72 along tissue wall 40, mutual magnetic attraction causes electrode assembly 74 to track automatically the position of assembly 72 to maintain optimal dynamic alignment of the electrical conductors while ablating the tissue.

Figure 13:
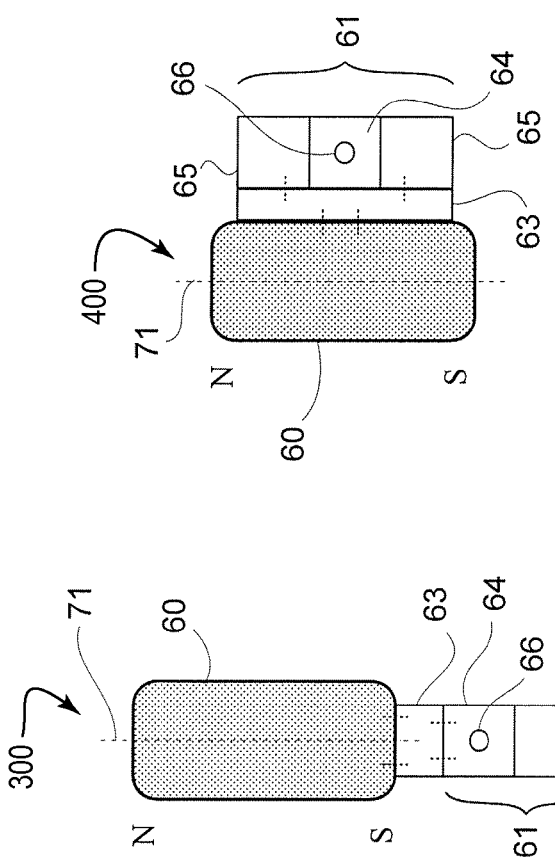
FIG. 13 is a top view of another embodiment of a magnetic electrode assembly for performing RF ablation, wherein a trailing elongated transmitting element is concentric with, or longitudinally aligned with, a slideable bar magnet.

FIG. 13 illustrates another embodiment of a magnetic electrode assembly 300. The assembly 300 includes components similar to those of assembly 200, and operates in similar fashion. The main difference is the orientation of electrical conductor 61 with respect to the magnetic core 60. Conductor 61 forms an elongated transmitting element or elongated conductive segment that at one end is bonded to and electrically insulated from core 60. Conductor 61 is oriented generally concentrically with, or stated otherwise, is aligned with, the longitudinal axis 71 and extends from core 60 in the longitudinal direction. As electrode assembly 300 is moved along a tissue wall, conductor 61 trails behind core 60 in concentric (or longitudinal) alignment therewith.

FIG. 14 illustrates another embodiment, 400, of an electrode assembly. This assembly includes components similar to those of assembly 200, and operates in similar fashion. In assembly 400, electrical conductor 61 forms an elongated conductive segment that is oriented generally parallel to the longitudinal axis 71 of magnetic core 60. Conductor 61 lies adjacent to core 60, and is bonded to and electrically insulated from the core by an insulator 63, using an adhesive, fasteners, or other means for connection. As electrode assembly 400 is moved along a tissue wall, conductor 61 rides alongside the core, generally parallel to axis 71.

Figure 15:
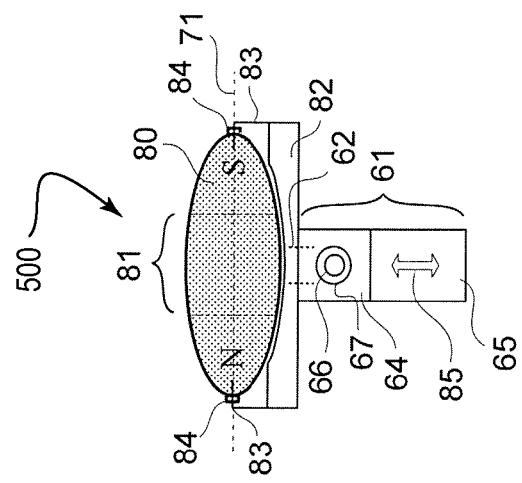
FIG. 15 is a top view of another embodiment of a magnetic electrode assembly for performing RF ablation, wherein the magnetic core forms a rolling ellipsoidal bar magnet.

FIG. 15 illustrates magnetic electrode assembly 500, which is another embodiment for performing precision RF ablation. Assembly 500 includes a rolling or rotatable bar magnet 80 having a smooth outer surface. A central area of the outer surface constitutes a circumferential magnetic coupling surface 81. In some embodiments, the bar magnet 80 may be cylindrical, and the magnetic coupling surface 81 may extend substantially from one longitudinal end of the bar magnet to the other longitudinal end thereof. In the illustrated embodiment, the bar magnet 80 has an ellipsoidal shape and volume, and the magnetic coupling surface 81 extends along only a portion of the longitudinal length of the bar magnet. An electrical conductor 61 is mechanically coupled to and electrically insulated from magnet 80, and includes a wire receiving terminal 64 and a transmitting element 65. Wire receiving terminal 64 includes a means 66 for electrically coupling an external wire to conductor 61. A mechanical linkage 67 connects assembly 500 to an intracorporeal positioning device. At all times during translation of the device and rotation of bar magnet 80, transmitting element 65 remains adjacent to a portion of the central area of the circumferential magnetic coupling surface 81.

Electrical insulation between bar magnet 80 and conductor 61 is provided by a dielectric insulator 82. The insulator 82 is preferably rigid so that it may be reliably mechanically fastened to conductor 61 using one or more fasteners 62. In addition, insulator 82 supports one or more axles 83 and one or more bearings 84. Axles 83 and bearings 84 allow bar magnet 80 to rotate freely about a central longitudinal axis 71 so that the assembly may roll or be rolled along the surface of operative tissue.

The agility of electrode assembly 500 may be advantageous in some situations for positioning the device for ablation. The assembly's ability to roll rather than slide across irregular areas of tissue wall, combined with the gradual curvature of its ellipsoidal surface make translation of the leading (rigidly linked) electrode across the operative tissue less susceptible to obstruction, while allowing the following (flexibly linked) electrode to more easily work its way into optimal alignment, as compared with some sliding embodiments. In an optimal alignment, the magnetic coupling surfaces 81 of the complementary pair are in direct opposition. In other respects, when magnetically coupled to a complementary electrode assembly, operation of electrode assembly 500 during an ablation procedure is similar to the operation of assemblies 100, 200, 300, 400.

Figure 16:
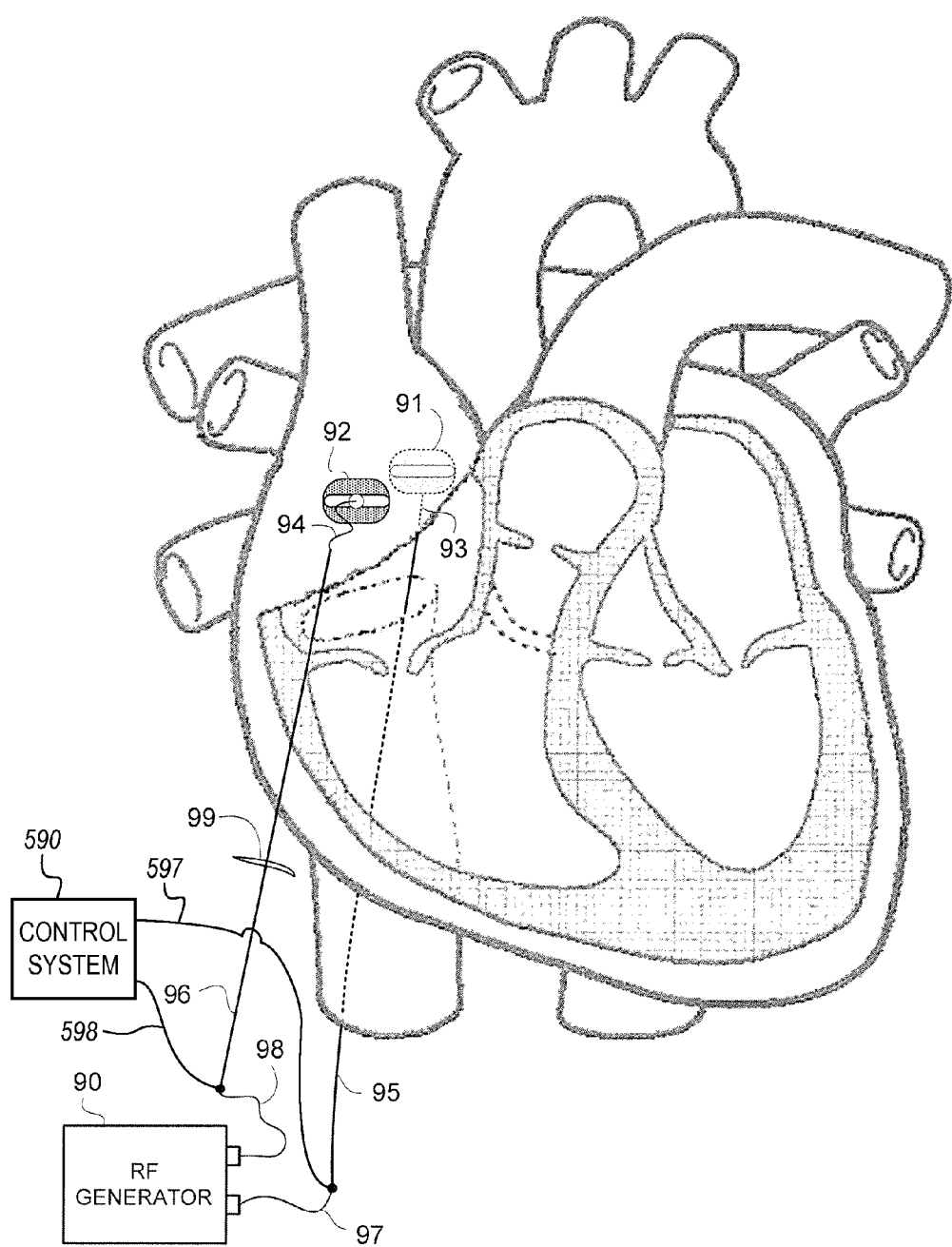
FIG. 16 is a frontal partial cutaway view of a human heart, showing an embodiment of a magnetically coupled ablation device positioned on opposite walls of the right atrium.

FIG. 16 is a conceptual illustration showing a magnetically coupled ablation device positioned on opposite walls of the right atrium of a human heart. The right atrium is shown only for purposes of illustrating procedural use of an embodiment, and is not meant to limit application thereof. For example, the illustrated embodiment has particular application in performing a maze procedure on the left atrium for isolating the pulmonary veins.

An endocardial magnetic electrode assembly 91 is equipped with a rigid mechanical linkage 93. Linkage 93 is coupled to an intracorporeal positioning device 95, preferably a stiff or somewhat flexible rod, hollow rod, or catheter. In some embodiments, the intracorporeal positioning device 95 can comprise a steering catheter, such as discussed further with respect to subsequent drawings. A wire 97 coupled to a wire receiving terminal on electrode assembly 91 runs through or along linkage 93 and positioning device 95, to a first terminal on an RF generator 90.

An epicardial magnetic electrode assembly 92 is equipped with a flexible mechanical linkage 94. Linkage 94 is coupled to a second intracorporeal positioning device 96, which may comprise a stiff or somewhat flexible rod or catheter. A second wire 98 is coupled to a wire receiving terminal on electrode assembly 92, and runs through or along linkage 94 and positioning device 96, to a second terminal on RF generator 90 to complete the circuit. The second terminal has an electrical polarity opposite that of the first terminal. RF generator 90 may be of any suitable variety. For example, in some embodiments, the generator 90 comprises a 200 W, 500 kHz to 1 MHz, 120/240 VAC unit such as a Boston Scientific model RF-3000 generator or equivalent. Wires 97 and 98 are sized appropriately to carry load current expected from such a device, and the wire receiving terminals on the electrode assemblies are configured for accommodating this size of wire.

The system is arranged so that a surgeon may initially position electrode assemblies 91 and 92 to approximate intracorporeal locations using minimally invasive techniques. For example, when positioning the device for transmural ablation of an atrial wall, assemblies 91 and 92 may be guided initially using hand-held or automatic intracorporeal positioning devices 95 and 96, respectively. Electrode 91 is shown positioned intravenously through the inferior vena cava to a location within the right atrium. Electrode 92 is shown positioned percutaneously through a small incision 99 made through the thoracic wall to a location on the outside of the right atrium. The length of positioning devices 95 and 96 will vary depending on type and application.

In achieving the initial approximate locations, it is contemplated that the surgeon will manually or automatically cause positioning devices 95 and 96 to transport the electrodes, simultaneously or one at a time, and in some instances, with the aid of one or more imaging devices providing feedback (e.g., live video feedback), until each electrode reaches a point close to the operative tissue. For example, when positioning the epicardial electrode, an endoscope may be used to provide a video image of the electrode and the surrounding tissue. When positioning the endocardial electrode, its position may be determined using fluoroscopy or may be inferred from electrical activity. An MRI or other image of the operative tissue, developed in advance of surgery, may be used as a map to assist the surgeon in identifying the correct approximate location for each electrode. When the approximate positions are achieved, the complementary electrode pair will be compelled into optimal alignment through mutual magnetic attraction, for example, in a manner such as previously described. At this point, the surgeon may proceed by making fine adjustments in the position of the leading electrode assembly (e.g., the assembly 91) to properly align it along a desired ablation path. For this purpose, an electrode assembly may further include a guiding feature, such as distinctive orientation indicia, or an indicator 85 (FIG. 15), such as a line or arrow, made from material easily discernable through the live video image that indicates to the surgeon the orientation of the transmitting element. For example, the indicator 85 may comprise any suitable radio-opaque material. This can assist the surgeon in properly orienting the electrode to draw an ablation scar along a desired pathway.

When the electrodes are in optimal alignment along the desired pathway, the surgeon may cause RF generator 90 to energize the electrical circuit and begin the process of burning transmural lesions into the tissue. After sufficient time has elapsed (e.g., about 1 minute, depending on heat transfer), the surgeon may deliberately cause the leading electrode to move further along the desired pathway so that the following electrode tracks the movement and maintains the device in optimal alignment, without excessive overlapping of tissue already burned. The procedure may be performed using continuous or intermittent application of RF current, and may be continued until a desired maze pattern has been achieved. In one application, a skilled surgeon may control the operation by guiding the complementary electrodes slowly and continuously along a desired burn path while continuously or intermittently applying RF current over the course of electrode movement.

Electrode assemblies 91 and 92 are each depicted as having a trough-type core similar to assembly 100. However, either or both electrode assemblies 91 and 92 may comprise alternative configurations according to the principles herein disclosed, such as one that incorporates a slideable cylindrical core, as shown in assemblies 200, 300, and 400, one that incorporates a rotatable ellipsoidal core, as shown in assembly 500, or some other configuration of an electrode assembly having a magnetic coupling surface electrically insulated from an electrical conductor having a wire receiving terminal and a transmitting element adjacent to the magnetic coupling surface, and a mechanical linkage to an intracorporeal positioning device. In still other or further embodiments, the electrode assemblies 91, 92 can resemble the electrode assemblies described below, including assemblies in which an electrode is not electrically insulated from a magnetic coupling surface, or is not electrically insulated from a magnetic member.

Certain embodiments may be used in connection with an external control system 590 that controls energy transmission between the transmitting elements of the electrode assemblies. The control system 590 may be electrically coupled with the assemblies 91, 92 via additional electrical leads 597, 598. The control system 590 may provide an optional safety feature that prohibits transmission of energy unless the ablation device is in optimal or near optimal alignment. One embodiment of this feature may be a current-limiting feature that interrupts the circuit when the peak current exceeds a predetermined threshold. Another embodiment may include a voltage-limiting feature that interrupts the circuit when the peak voltage required to sustain current flow between the electrodes exceeds a predetermined threshold. Another embodiment of this feature may rely on a proximity sensor located on one or both of the complementary electrode assemblies that senses an optimal alignment condition or absence thereof. For example, an electrode assembly may include a miniaturized reed switch that changes electrical state in response to a magnetic field strength that exists only when both complementary cores are closely or optimally aligned. A DC signal indicating the position of the reed switch may be superimposed on a wire carrying RF (e.g., one of the wires 97, 98), or an additional isolated wire (e.g., one of the wires 597, 598) may threaded through the respective intracorporeal positioning device 95, 96 to carry the reed switch signal to the external control system 590. In this fashion, the control system 590 can independently verify whether the ablation device is in optimal alignment, and allow energy transmission only when this condition exists. The safety feature thereby helps to prevent unnecessary damage to tissue surrounding the desired ablation path.

In some embodiments, the control system 590 may have the RF generator 90 incorporated therein. In further embodiments, only a single set of wires 97, 98 may be used with the magnetic electrode assemblies 91, 92. In some embodiments, the control system 590 and magnetic electrode assemblies 91, 92 can operate in a mapping mode, rather than an ablation mode. For example, in some embodiments, the conductors 17, or specifically, the transmitting elements 21, of the magnetic electrode assemblies 91, 92 can be used to detect electrical properties of the tissue positioned between them, rather than to ablate the tissue. For example, in some embodiments, the electrodes of the electrode assemblies 91, 92 can be used to determine a conductance of the tissue wall that is positioned between the electrodes. Any suitable mapping procedure or technique may be accomplished via the control system 590.

The electrodes of the magnetic electrode assemblies 91, 92 can be used to monitor one or more electrical properties of the tissue during an ablation procedure. In some embodiments, a single set of wires 97, 98 may be used both to deliver the RF energy to the electrodes and to monitor the conductance, and/or other suitable electrical property, of the tissue that is positioned between the electrodes. In other embodiments, a first set of wires 97, 98 can be used to deliver the RF energy, while a second set of wires 97, 98 can be used to monitor the one or more electrical properties of the tissue. Electrical properties of the tissue can change during an ablation procedure due to the killing of tissue cells. Accordingly, progress of the ablation procedure may be determined, at least in part, from alteration of the electrical properties of the tissue. Monitoring the one or more electrical properties (e.g., conductance) can provide feedback information from which it can be determined whether to adjust the delivery of energy to the ablating electrodes, such as by adjusting one or more of the frequency, amplitude, duration, and/or other suitable properties of the signals being delivered via the RF generator 90. In various implementations, at least some of the foregoing monitoring and adjustment procedures can be performed via the control system 590 (e.g., whether manually or automatically). For example, in some embodiments, the control system 590 can measure power output of the RF generator 90. At a given voltage between the electrodes, the tissue will permit a given level of current to travel between the electrodes. However, as the cells of the tissue are damaged, the conductivity of the tissue can be diminished, and thus the current level likewise diminishes. The control system 590 can monitor the change in the power output, as correlated with the change in the current level and/or the rate of change of the power output, as correlated with the rate of change of the current level.

It is also contemplated that embodiments of an electrode assembly may include one or more inductive conductors oriented with respect to the magnetic core to form an electromagnet, such that energization of the inductive conductor with a DC current amplifies the magnetic field. In other or further embodiments, the permanent magnet cores discussed above can be augmented or replaced by such electromagnets. In certain embodiments, an electromagnet-based design could permit for adjustment of the magnetic field strength by the control system 590. For example, if the electrode assemblies are having difficulty aligning due to gravity, atrial wall topography, or some other obstruction, the control system may temporarily boost the strength of the magnetic field by adding or elevating DC current flow through the inductive conductor, up to a safe limit, until acceptable alignment is achieved. An additional isolated wire may be provided for energizing the inductive conductor. The control system may also allow the temporary boost to be initiated through manual action.

At least some of the stages of any of the foregoing procedures can be accomplished via the control system 590. In some embodiments, the control system 590 can comprise a general-purpose or special-purpose computer, or some other electronic device, and at least a portion of the procedures may be embodied in machine-executable instructions therein. In other embodiments, at least a portion of the procedures (e.g., various steps or stages thereof) may be performed by hardware components that include specific logic for performing the steps or by a combination of hardware, software, and/or firmware.

As can be appreciated from the foregoing, a variety of electrode assembly arrangements are possible. For example, various electrode assemblies 30, 50, 72, 74, 91, 92, 200, 300, 400, and 500 are depicted in the drawings and are described in the foregoing written disclosure. Certain electrode assemblies can be well-suited to cooperate with each other in endocardial and epicardial arrangements, where one electrode assembly is at an interior of a wall of the heart and another electrode assembly is at an exterior thereof. The foregoing description includes discussions of how certain arrangements can assist in aligning one of the endocardial and epicardial electrode assemblies with the other electrode assembly.

Together, a pair of endocardial and epicardial electrode assemblies can function as a bipolar ablation system. Stated otherwise, various embodiments of bipolar ablation systems can include a pair of complementary electrode assemblies, such as any suitable combination of those assemblies described above, which can be coupled with each other at opposite sides of a wall of the heart. As used herein, the term "coupled" and variants thereof are used in their ordinary sense, and include any suitable form of interaction between two or more entities, including mechanical, electrical, magnetic, electromagnetic, fluid, and thermal interaction. The terms connote some form of connection or interaction, although two components may be coupled to each other without being in direct contact with each other. Accordingly, one electrode assembly can be magnetically coupled with another electrode assembly across a wall of the heart, such as when one electrode assembly automatically aligns with and/or tracks the position of the other electrode assembly.

Additional ablation systems and electrode assemblies are discussed hereafter. Although numbering relative to the additional systems and assemblies may differ from that provided with respect to the foregoing embodiments, it should be understood that the systems and assemblies can resemble those previously depicted and described, in certain respects. Relevant disclosure set forth above regarding similar features thus may not be repeated hereafter. Any suitable combination of the features and variations of the same described with respect to the following systems and assemblies can be employed with any of the assemblies and systems described above, and vice versa.

Figure 17:
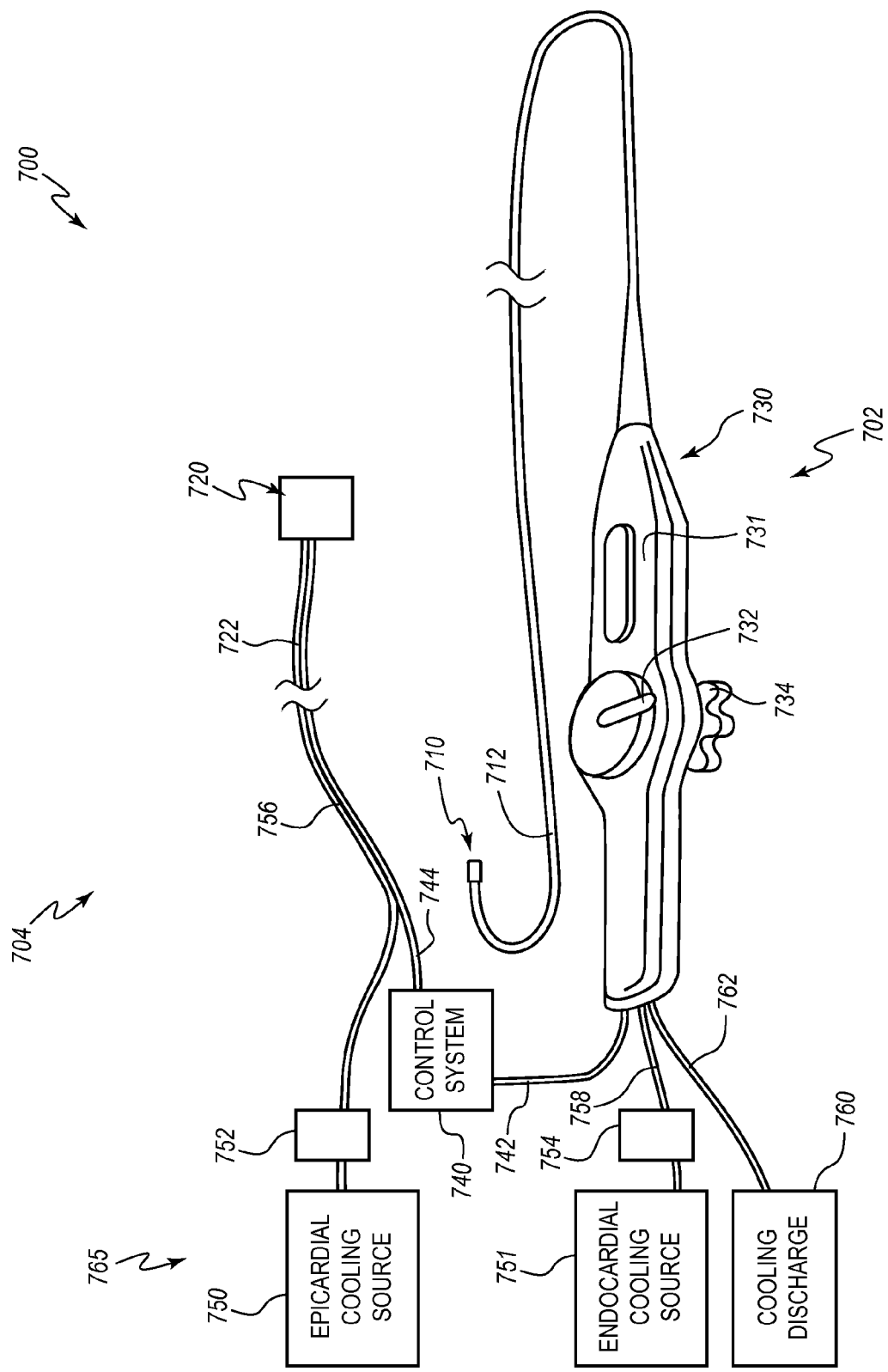
FIG. 17 is a schematic view of an embodiment of a magnetic coupling system that can be used for ablating tissue.

FIG. 17 illustrates an embodiment of a magnetically coupling system 700 that is configured for use at opposite sides of a tissue structure, such as an atrial wall, in one or more operational modes, such as, for example, an ablative mode or a mapping mode. The magnetically coupling system 700 includes a primary or leading assembly 702 and a secondary, following, or tracking assembly 704. In the illustrated embodiment, which is further discussed with respect to FIGS. 18A-21B, the leading assembly 702 can be used at endocardial positions, and the tracking assembly 704 can be used at opposing epicardial positions. Accordingly, the leading assembly 702 may also be referred to herein as an endocardial assembly, and the tracking assembly 704 may also be referred to herein as an epicardial assembly.

The leading assembly 702 can include a leading magnetic electrode assembly 710, which can be secured to an intracorporeal positioning device 712. The device 712 may also be referred to as a linkage, and it may be attached to the assembly 710 in any suitable manner. The tracking assembly 704 can include a tracking magnetic electrode assembly 720, which can be secured to an intracorporeal positioning device 722, or linkage, in any suitable manner. The positioning device 722 can, for example, comprise a catheter or the like. In various embodiments, the magnetic electrode assemblies 710, 720 can resemble any of the magnetic electrode assemblies previously discussed. However, the illustrated magnetic electrode assemblies 710, 720 will be discussed in greater detail below.

The intracorporeal positioning device 712 of the leading assembly 702 can comprise any suitable probe or catheter arrangement. In the illustrated embodiment, the intracorporeal positioning device 712 comprises a steering catheter. Any suitable steering catheter arrangement is possible. For example, suitable steering catheter arrangements are disclosed in U.S. Pat. No. 7,938,828, titled COOLED ABLATION CATHETER, which issued on May 10, 2011, the entire contents of which are hereby incorporated by reference herein. The steering catheter can aid a practitioner in positioning the leading magnetic electrode assembly 710 at a desired location and in a desired orientation within the patient, and/or may aid in movement of the leading magnetic electrode assembly 710 during a procedure (e.g., ablation or mapping procedure).

The leading assembly 702 can include a steering assembly 730 that is configured to effect movement of the magnetic electrode assembly 710 at the distal end of the catheter 712. The steering assembly 730 can include a handle 731, a steering lever 732, and a locking lever 734.

Figure 18A:
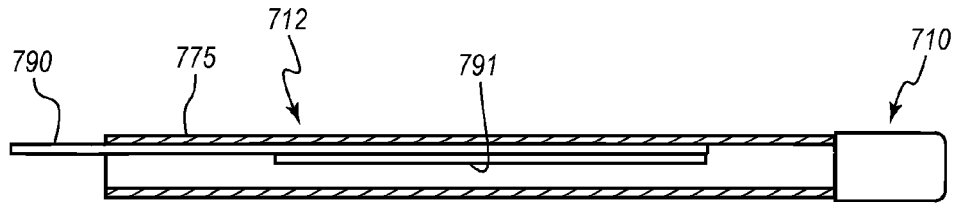
FIGS. 18A-18C are cross-sectional views of an embodiment of a steering catheter that is compatible with the system of FIG. 17, wherein the steering catheter is shown in various orientations to which it can be moved via a steering wire.
Figure 18B:
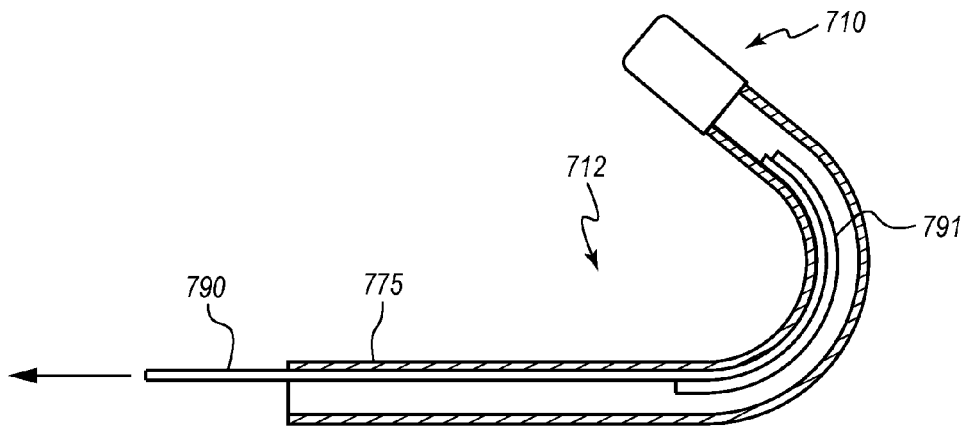
Figure 18C:
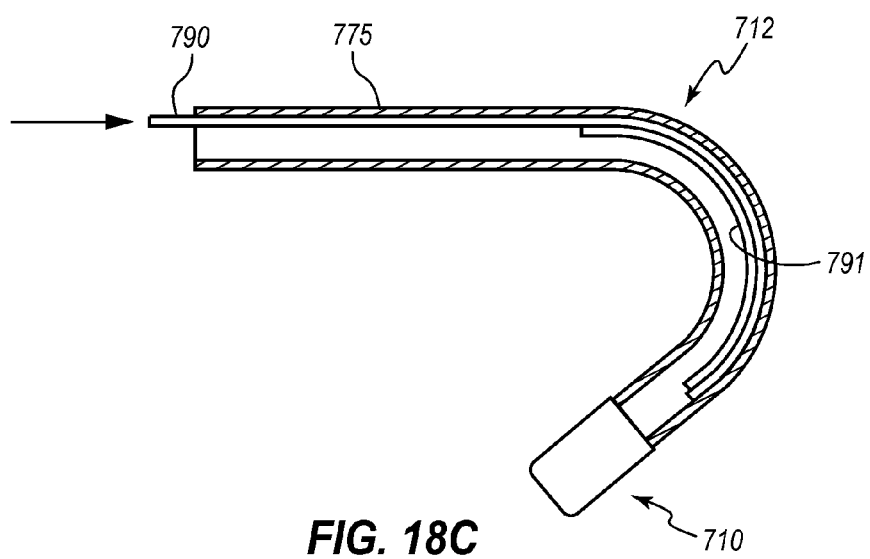

With reference to FIGS. 18A-18C, the steering assembly 730 can further include one or more steering wires 790 and a spring element 791. FIGS. 18A-18C depict cross-sectional views of a distal end of the catheter 712 in various orientations. For the sake of clarity, various features of the catheter 712 that are not part of the steering assembly 730 are not shown in these views. The spring element 791 can be attached to or otherwise coupled with a sheath 775 portion of the catheter 712, such that movement of the spring element 791 effects a corresponding movement of the catheter 712, and such that an orientation of the spring element 791 results in a corresponding orientation of the catheter 712. Other arrangements are also possible, including arrangements that might not employ a spring element.

In the illustrated embodiment, the steering assembly 730 includes a single steering wire 790 that is connected to the steering lever 732 at a proximal end thereof and that is connected to one side of the spring element 791 at a distal end thereof. In use, the steering lever 732 can be rotated relative to the handle 731 so as to move the steering wire 790 relative to the spring element 791. The locking lever 734 may be used to fix a position of the steering lever 732 relative to the handle 731, and thereby fix a position of the steering wire 790 relative to the spring element 791 so as to maintain a desired configuration of the distal end of the catheter 712. Orientation of the catheter 712 in this manner can be used to provide a desired orientation of the magnetic electrode assembly 710. Other embodiments can include two steering wires 790, with each wire being connected to opposite sides of the spring element 791.

FIG. 18A illustrates a natural or relaxed orientation of the catheter 712 in which the steering wire 790 neither compresses nor extends one side of the spring element 791. In such an arrangement, the catheter 712 may be substantially linear.

FIG. 18B illustrates an orientation to which the catheter 712 can be transitioned by rotating the steering lever 732 so as to move the steering wire 790 in the proximal direction, as illustrated by the arrow. Such movement can compress an upper side of the spring element 791, causing the catheter 712 to curve in a first direction. In such an orientation, the catheter 712 may be substantially J-shaped.

FIG. 18C illustrates an orientation to which the catheter 712 can be transitioned by rotating the steering lever 732 so as to move the steering wire 790 in the distal direction, as illustrated by the arrow. Such movement can extend an upper side of the spring element 791, causing the catheter 712 to curve in a second direction that is opposite the first direction depicted in FIG. 18B. The catheter 712 may again define a J-shape in this orientation. Any other suitable steering catheter arrangement is contemplated.

With reference again to FIG. 17, the system 700 can include a control system 740, which can be electrically coupled with the leading assembly 702 via an electrical cable 742, and which can be electrically coupled with the tracking assembly 704 via another electrical cable 744. In the illustrated embodiment, the electrical cable 742 terminates at the steering assembly 730, but the cable 742 includes one or more electrical leads 774 that extend through the assembly 730 and the catheter 712 so as to be coupled with the leading magnetic electrode assembly 710 at the distal end of the catheter 712 (see FIG. 20). In the illustrated embodiment, a distal portion of the electrical cable 744 defines a portion of the catheter 722 that is coupled with the tracking magnetic electrode assembly 720.

The control system 740 can resemble the control system 590 discussed above, and can be configured to function in any of the manners described with respect thereto. For example, in various embodiments, the control system 740 can comprise an RF generator, and can be configured to deliver electrical (e.g., RF) signals to or through the magnetic electrode assemblies 710, 720, such as in a bipolar RF ablation procedure. In other or further embodiments, the control system 740 can be configured to operate in a mapping mode, and can receive electrical signals from the magnetic electrode assemblies 710, 720 so as to map electrical properties of a tissue structure that is positioned between them. In still other or further embodiments, the control system 740 can be configured to monitor an electrical conductance, and/or other electrical property, between the electrode assemblies 710, 720 while electrical energy is communicated through the tissue wall, and in further embodiments, the control system can adjust an amount of energy delivered to the electrode assemblies 710, 720 in response to a measured level of the electrical conductance and/or other electrical property.

With continued reference to FIG. 17, the system 700 can be configured to cool one or more electrodes that are used in an ablative procedure. In the illustrated embodiment, the system 700 is configured to cool both electrodes—one in each of the magnetic electrode assemblies 710, 720. The system 700 includes an epicardial cooling source 750 and an endocardial cooling source 751, each of which may include a reservoir of any suitable cooling medium. In some embodiments, each of the cooling sources 750, 751 may utilize the same cooling medium, whereas in other embodiments, the cooling media may be different. In certain embodiments, the cooling medium can comprise any suitable fluid (i.e., liquid and/or gas). As further discussed below, in some embodiments, at least one of the cooling media (e.g., the cooling media of the epicardial cooling source 750) comprises a liquid that is introduced into the patient at the position of the electrode, and thus the liquid may be biocompatible. For example, the liquid may comprise saline. In other or further embodiments, at least one of the cooling media (e.g., the cooling media of the endocardial cooling source 751) comprises a liquid that might be preferable not to introduce into the body of the patient. In some embodiments, one or both of the leading and tracking assemblies 702, 704 operates as a closed cooling system, in which the cooling medium is not introduced into the patient, but is instead is delivered to the electrode and then returned from the electrode. In other or further embodiments, one or both of the leading and tracking assemblies 702, 704 operates as an open cooling system, in which the cooling medium is introduced into the patient. In the illustrated embodiment, the endocardial assembly 702 operates as a closed cooling system and the epicardial assembly 704 operates as an open cooling system, as discussed further below.

The system 700 can include one or more cooling discharges 760, which may be used to collect the cooling medium that is returned from an electrode. In the illustrated embodiment, only a single cooling discharge 760 is used to receive cooling fluid that has been heated by the endocardial magnetic electrode assembly 710. In some embodiments, the cooling discharge 760 may cool the used cooling medium and cycle it back to the cooling source 751.

In the illustrated embodiment, the cooling source 751 is configured to deliver cooling medium to the magnetic electrode assembly 710 via a fluid conduit 758, and the cooling source 750 is configured to deliver cooling medium to the magnetic electrode assembly 720 via a fluid conduit 756. In the illustrated embodiment, separate pumps 752, 754 are used to force the cooling medium through the fluid conduits 756, 758, respectively. In the illustrated embodiment, an additional fluid conduit 762 is used to conduct spent cooling medium from the electrode assembly 710 to the cooling discharge 760. The cooling sources 750, 751, cooling discharge 760, pumps 752, 754, and fluid conduits 756, 758, 762 may be referred to as a cooling system 765. Any suitable cooling system 765 may be used with the magnetically coupling system 700. For example, suitable cooling systems are disclosed in U.S. Pat. No. 7,938,828, which is incorporated by reference above.

In the illustrated embodiment, the cooling system 765 is independent of the control system 740. In other embodiments, the control system 740 may be interoperable with the cooling system 765. For example, in some embodiments the control system 740 may control and/or otherwise communicate with the cooling system 765. For example, in some embodiments, the electrode assemblies 710, 720 may include temperature sensors that detect the temperature at or near the electrodes. The temperature sensors can be configured to communicate temperature information to the control system 740. Based on the temperature information thus received, the control system 740 can adjust operation of the cooling system 765, such as by increasing or decreasing a flow rate of the cooling medium through the conduits 746, 758, 762.

Figure 19:
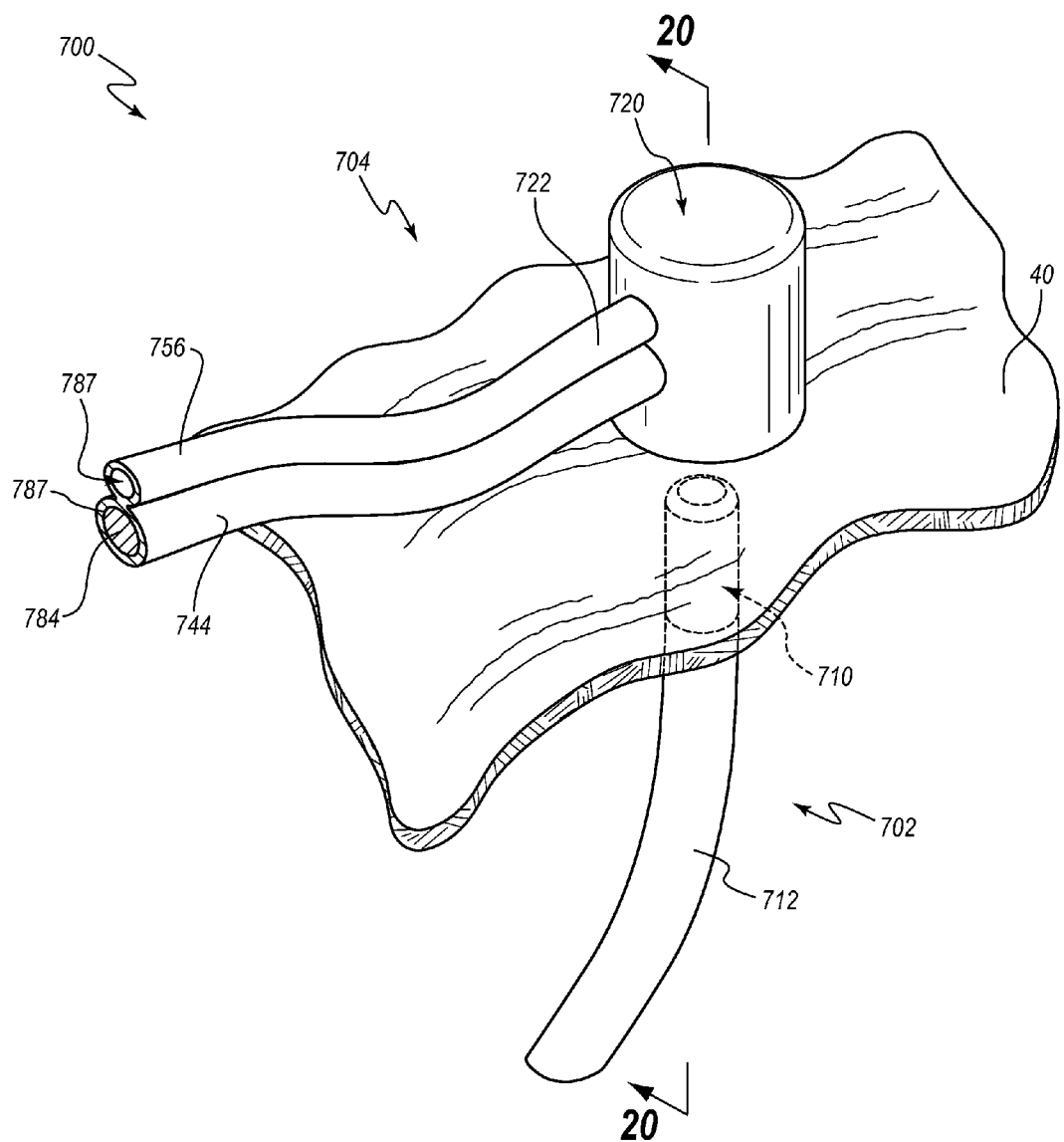
FIG. 19 is a perspective view of a distal portion of the system of FIG. 17 shown coupled across an atrial wall.
Figure 20:
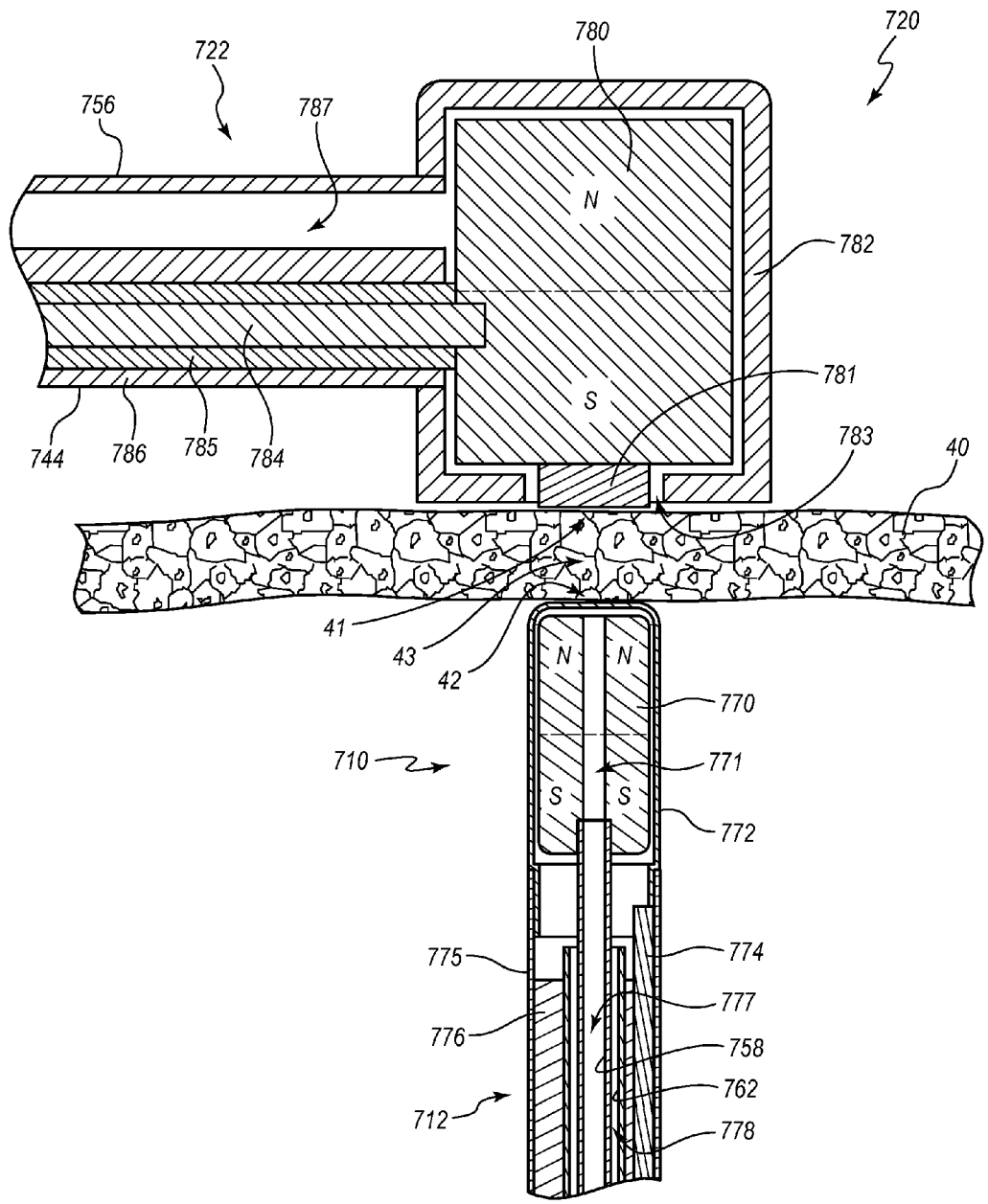
FIG. 20 is a cross-sectional view of the portion of the system shown in FIG. 19, taken along the view line 20-20.
Figure 21:
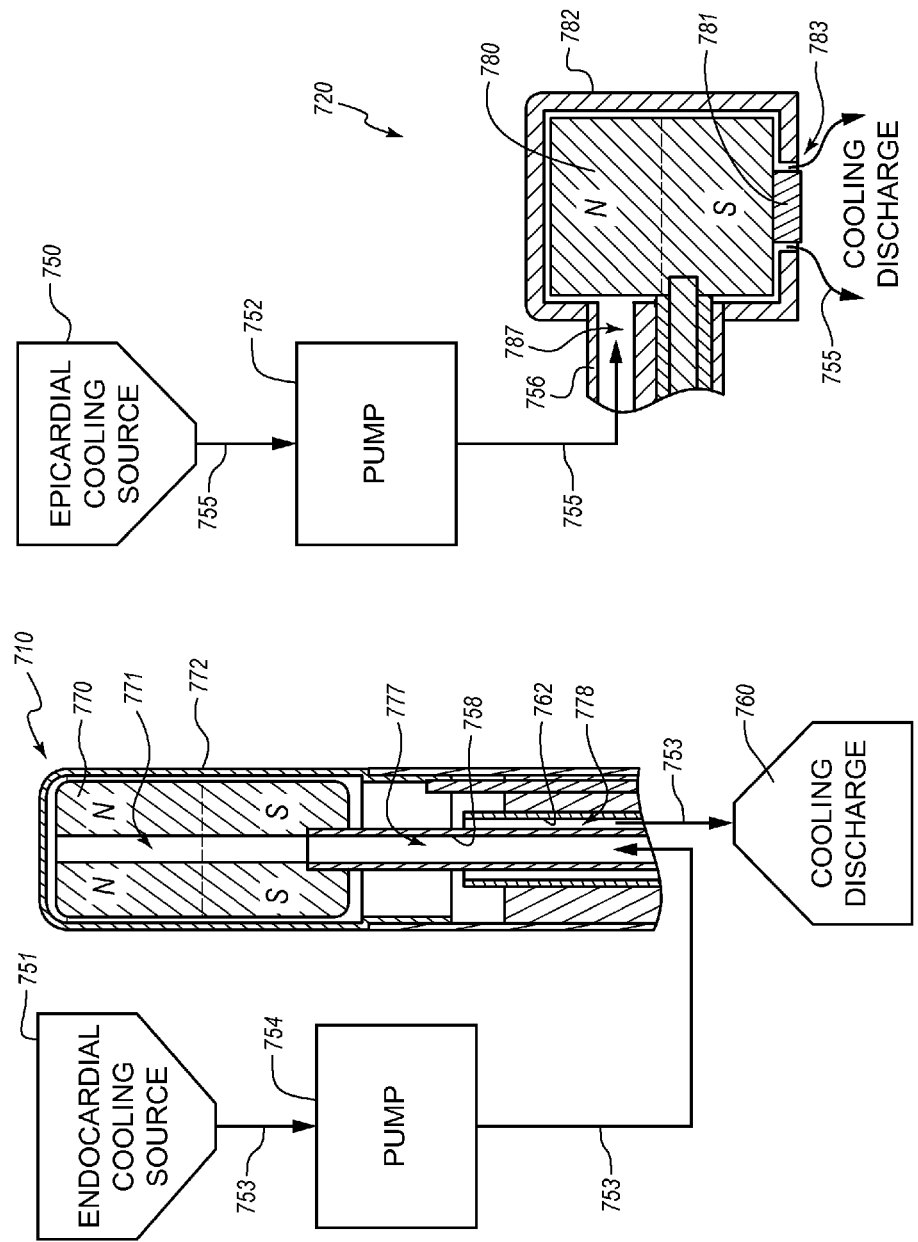
FIG. 21A is a schematic view of an embodiment of a cooling system that is used to cool an electrode assembly.
FIG. 21B is a schematic view of another embodiment of a cooling system that is used to cool another embodiment of an electrode assembly, wherein the electrode assemblies of FIGS. 21A and 21B are compatible with the system of FIG. 17.

FIGS. 19 and 20 depict the distal end of the system 700 in use. As illustrated, the system 700 is operating in a mapping mode. As further discussed below, the system 700 may have a similar configuration when operating in an ablation mode.

The leading system 702 is positioned at an interior side of the atrial wall 40. In particular, the steering catheter 712 has been positioned such that a distal tip of the magnetic electrode assembly 710 is flush against an inner surface of the atrial wall 40. Movement of the leading magnetic electrode assembly 710 along the inner surface of the atrial wall 40 causes the tracking magnetic electrode assembly 720 to automatically follow—or move concurrently with—the assembly 710 along the outer surface of the atrial wall 40. In some embodiments, the steering catheter 712 may be relatively stiff or rigid, whereas the positioning device 722 can be relatively flexible.

With reference to FIG. 20, in the illustrated embodiment, the magnetic electrode assembly 710 includes a magnetic member 770 and an electrode 772. The magnetic member 770 can comprise a magnetic source, such as any of the magnetic sources discussed above. In the illustrated embodiment, the magnetic member 770 comprises a permanent magnet that provides a magnetic field. The north and south poles N, S of the permanent magnet are identified, although other orientations are possible. In other embodiments, the magnetic member 770 may instead include a magnetically influenced material, such that the magnetic member 770 does not produce a magnetic field.

In the illustrated embodiment, the magnetic member 770 is substantially cylindrical and is elongated in a longitudinal direction. The magnetic member 770 defines a fluid channel 771 that extends through a full length of the magnetic member 770 along a longitudinal axis thereof. A proximal end of the magnetic member 770 is coupled with the fluid conduit 758 in any suitable manner, and may form a fluid-tight seal therewith.

In the illustrated embodiment, the electrode 772 encompasses, envelopes, or encases the magnetic member 770. However, a small gap or volume, or one or more channels, can be provided between the electrode 772 and the magnetic member 770 through which a cooling medium can be permitted to pass. In some embodiments, the electrode 772 can be electrically insulated from the magnetic member 770. For example, one or more dielectric spacers (not shown) can maintain an air gap between the electrode 772 and the magnetic member 770, and the cooling medium may be of a non-conducting variety. However, in other embodiments, the electrode 772 may be permitted to electrically communicate with the magnetic member 772. For example, in some embodiments, the cooling medium may comprise a conductive fluid (e.g., saline solution), which may be capable of carrying a current between the electrode 772 and the magnetic member 770. In other or further embodiments, the electrode 772 and the magnetic member 770 may be in electrical communication with each other in the absence of a conducting fluid.

The steering catheter 712 can include the sheath 775, which may comprise a dielectric material. The catheter 712 can further include an insulating layer 776 of any suitable material, which may also be a dielectric material. In the illustrated embodiment, the wire or electrical lead 774 extends between the sheath 775 and the insulating layer 776, and a distal end thereof is electrically connected to a proximal end of the electrode 772. The steering catheter 712 can further include the fluid conduits 758, 762, as previously discussed. In the illustrated embodiment, the fluid conduits 758, 762 are concentric, with the fluid conduit 758 being positioned at an interior of the fluid conduit 762. The fluid conduit 758 defines a lumen 777 through which the cooling medium can flow into the channel 771 of the magnetic member 770. The fluid conduit 762 likewise defines a lumen 778 through which the cooling medium can flow after it has extracted heat from the electrode 772.

With continued reference to FIG. 20, the tracking magnetic electrode assembly 720 can include a magnetic member 780 and an electrode 781. The magnetic member 780 can comprise a magnetic source, such as a permanent magnet. In the illustrated embodiment, the north and south poles N, S of the permanent magnet are identified, although other orientations are possible. The poles can be oriented so as to attract the magnetic member 770 of the magnetic electrode assembly 710. In the illustrated embodiment, the magnetic member 780 is substantially cylindrical and defines a central longitudinal axis. In some embodiments, alignment of the central longitudinal axis of the magnetic member 780 and that of the magnetic member 770 can yield a strong magnetic coupling, such that the magnetic member 780 can automatically move relative to the magnetic member 770 so as to achieve or maintain, or so as to move toward, an alignment of the central longitudinal axes. In the illustrated embodiment, the magnetic member 770 is larger than the magnetic member 780, and has a stronger magnetic field than that of the magnetic member 770. Other arrangements are also possible.

The magnetic member 780 can be electrically coupled with the electrode 781. For example, in some embodiments, the magnetic member 780 comprises a material that is both conductive and permanently magnetic, such as, for example, magnetized iron. The electrode 781 can comprise any suitable material, such as those described above with respect to other electrodes, and in some embodiments, the electrode comprises a non-magnetic material. Other embodiments may be devoid of a separate electrode 781. For example, the magnetic member 780 may function as both the magnetic member and as the electrode. The magnetic member 780 may define a tiered shape of concatenated cylinders (such as that depicted in FIG. 20 with respect to the magnetic member 780 and the electrode 781), a unitary cylinder, or any other suitable shape or configuration.

The magnetic member 780 can be electrically coupled with a distal end of a wire or electrical lead 784, which can be coupled with the control system 740 (FIG. 17) at its proximal end. A sheath or casing 782 can encompass, envelope, or encase the magnetic member 780. A small gap or volume, or one or more channels, can be provided between the electrode casing 782 and the magnetic member 780 through which a cooling medium can be permitted to pass. The casing 782 can comprise an electrically insulating material, and thus can define or restrict an electrical pathway between the electrodes 772, 781 and, in some embodiments, an electrical pathway between the electrode 772 and the magnetic member 780. Stated otherwise, the casing 782 can focus electrical energy that is transmitted between the electrodes 772, 781 and/or the electrode 772 and the magnetic member 780.

In some embodiments, the casing 782 defines an aperture or port 783 through which cooling medium can exit the casing 782. In the illustrated embodiment, the electrode 781 extends through the port 783 such that the casing encompasses the electrode 781. Cooling medium thus can readily contact that electrode 781 about its periphery so as to cool the electrode 781.

The intracorporeal positioning device 722 can include at least a portion of the fluid conduit 756 and at least a portion of the electrical cable 744. In the illustrated embodiment, the fluid conduit 756 and the cable 744 define discrete lobes, whereas in other embodiments, the conduit 756 and the cable 744 can be incorporated into a single cylindrical structure. In the illustrated embodiment, a single sheath 786 encompasses the conduit 756 and the cable 744. The conduit 756 defines a lumen 787 through which cooling medium can be introduced into the magnetic electrode assembly 720. The cable 744 can include a layer of insulation 785.

As previously mentioned, the control system 740 (FIG. 17) can be used to energize the electrodes 772, 781 so as to ablate the atrial wall 40. In other or further embodiments, the control system 740 can be used to map the atrial wall 40. In some implementations, the mapping can include receiving, monitoring, or measuring one or more electrical signals from an endocardial surface, or from the endocardium 42, via the electrode 772. The electrical signals may correspond to the voltage of the portion of the endocardial tissue that is in contact with the electrode 772, with respect to some reference voltage (e.g., a ground voltage). For example, the reference voltage may be relative to some other portion of a patient and may be obtained using a dedicated reference electrode or another measurement electrode. Accordingly, in some implementations, the mapping can comprise measurement of the electrical properties of the endocardium 42.

In other or further implementations, the mapping can include receiving, monitoring, or measuring one or more electrical signals from an epicardial surface, or from the epicardium 41, via the electrode 781. The electrical signals may correspond to the voltage of the portion of the epicardial tissue that is in contact with the electrode 781, with respect to some reference voltage (e.g., a ground voltage), which may be obtained using a dedicated reference electrode or another measurement electrode. Accordingly, in some implementations, the mapping can comprise measurement of the electrical properties of the epicardium 41. Moreover, in certain of such implementations, the same reference voltage may be used for both the endocardial and epicardial mapping. In other or further implementations, the endocardial and epicardial mapping may occur simultaneously and/or may occur dynamically as the electrode assemblies 710, 720 are moved in tandem relative to the atrial wall 40.

In yet other or further implementations, the mapping can include determining, monitoring, or measuring electrical properties of the portion of the atrial wall that is positioned between the electrodes 772, 781, which may also be referred to as determining, monitoring, or measuring electrical signals between the electrodes 772, 781. Such mapping may be particularly useful in determining the electrical properties of the mid-myocardium 43. The mapping can comprise determining or monitoring a voltage difference between the electrodes 772, 781 when the electrodes are in contact with opposing surfaces of the atrial wall 40. The myocardial mapping may take place dynamically as the electrode assemblies 710, 720 are moved in tandem relative to the atrial wall 40. Mapping the differences in sensed electrical potentials between the electrodes 772, 781 may be useful in determining regions of the atrial wall 40 at which ablative treatment is desirable. It is noted that the foregoing mapping procedures, which are discussed with respect to the control system 740 and the electrodes 772, 781, may also be employed with other control systems (e.g., the control system 590) and electrode assemblies (e.g., the electrode assemblies 91, 92) disclosed herein.

FIGS. 21A and 21B illustrate cooling of the magnetic electrode assemblies 710, 720 during an ablation procedure.

With reference to FIG. 21A, a cooling medium 753 can be delivered from the endocardial cooling source 751 via the pump 754, and can further be urged through the lumen 777 of the fluid conduit 758 into the lumen 777 of the magnetic member 770. The cooling medium 753 can then exit the lumen 777 and flow about an exterior of the magnetic member 770 and against an interior surface of the electrode 772 so as to cool the electrode 772. The cooling medium 753 can then be channeled from the magnetic electrode assembly 710 through the lumen 778 of the fluid conduit 762 and to the cooling discharge 760.

With reference to FIG. 21B, a cooling medium 755 can be delivered from the epicardial cooling source 750 via the pump 752, and can further be urged through the lumen 787 of the fluid conduit 756. The cooling medium 755 can exit the lumen 787 and flow about an exterior of the magnetic member 780 and against an interior surface of the casing 782. The cooling medium 755 can cool the electrode 781 as it flows about a perimeter thereof through the port 783. At least a portion of the cooling medium 755 may evaporate and/or may flow into the region of the ablation site.

With reference again to FIG. 20, in the illustrated embodiment, one or both of the electrodes 772, 781 may directly contact the atrial wall 40 during an ablation procedure. Cooling of the electrodes 772, 781, as just described, can be advantageous in situations where it is desirable to prevent or inhibit tissue ablation at the portion or surface of the electrode that contacts the tissue. During ablation, the surface temperature of the electrode can elevate such that the temperature of the tissue that is contacted by the electrode may be raised to a temperature that injures or damages the tissue (e.g., a temperature above about 42 degrees Celsius). Cooling the electrode thus can reduce undesired tissue injury at the surface, either when the electrodes are used in a static mode, which may also be referred to as a static ablation mode, or in a dynamic mode, which may also be referred to as a dynamic tracking mode or a dynamic ablation mode. The various operational modes are discussed further below. It can be desirable for the surfaces of the electrodes that are in contact with the tissue to be at low temperatures, as this can also result in higher actual temperatures below the surface of the tissue. In some embodiments, the temperatures of the electrodes may be monitored, such as via any suitable temperature sensor coupled therewith (e.g., one or more thermocouples). Operation of the cooling system 765 may be adjusted in response to the temperatures observed via the temperature sensors. Ablation of the tissue thus may permit ablation to occur deeper within the atrial wall 40—such as at a position that is between, and centrally located relative to, the opposing electrodes—while reducing tissue damage at the surface of the atrial wall 40.

Stated otherwise, cooling can cause the electrode-tissue interface to have lower temperature values. As a result, the hottest isothermal region resulting from energizing the electrodes 772, 781 can be shifted deeper into the tissue. This likewise shifts the boundary of tissue that is rendered nonviable by ablation deeper into the atrial wall 40. An electrode that is actively cooled can be used to transmit more ablation energy into the tissue, as compared with the same electrode in a non-cooled state. With cooling, the lesion formed by ablation extends deeper into the tissue and has a larger volume. Larger lesions may be more effective in blocking undesired electrical signals that are responsible for AF and/or can reduce the number of passes or energizations of the electrodes 772, 781 along the atrial wall 40 in forming the electrical barrier lesions.

As can be appreciated from earlier discussion, in some procedures, the electrodes 772, 781 are operated in a static mode, or static ablation mode, in which they are positioned on opposite sides of the atrial wall 40, and then the electrodes are energized with RF energy while the electrodes remain in a relatively fixed position relative to each other and relative to the atrial wall 40. After ablation is conducted at one ablation site, the electrodes 772, 781 are moved to another site, and the ablation procedure is repeated. In other or further procedures, the electrodes 772, 781 may instead operate in a dynamic mode so as to perform dynamic ablation. The dynamic mode may also be referred to as a dynamic ablation mode or as a dynamic tracking mode. In such procedures, the electrodes 772, 781 may remain in a generally fixed relationship relative to each other, but the electrodes may be moved (e.g., continuously moved) relative to the atrial wall 40 as RF energy is applied. As previously noted, in some instances, the electrode 772 may be moved by a practitioner, and the electrode 781 can automatically follow, or concurrently trace a substantially parallel path relative to, the electrode 772 due to the magnetic coupling of the electrode assemblies 710, 720. As can be appreciated, in certain embodiments, the electrode assemblies 710, 720 do not clamp the atrial wall 40 between them when operating in the dynamic mode, as the electrode assemblies 710, 720 are able to move relative to the atrial wall 40 in this mode. Stated otherwise, the magnetic attraction between the electrode assemblies 710, 720 can be sufficiently strong to maintain contact between the electrodes 772, 781 and the atrial wall 40 so as to facilitate communication of energy through the atrial wall, but may be sufficiently weak to permit the first and second assemblies to move relative to the atrial wall during ablation. In either the static or the dynamic modes, tissue injury may be reduced by cooling the electrodes. Moreover, in certain implementations, cooling of the electrodes may have a greater effect when operating in a static mode as compared to operating in a dynamic mode, depending on the temperature of the electrodes 772, 781 and the rate at which the electrodes 772, 781 are moved.

In some embodiments, cooling the magnetic electrode assemblies 710, 720 may desirably prevent one or more of the magnetic members 770, 780 from reaching the Curie temperature, where the magnetic properties of the magnetic members can be affected. In some embodiments, passing the cooling medium over an exterior surface of the electrode (such as the electrode 781 in the illustrated embodiment) can clean the electrode or otherwise clear debris from the electrode that might inhibit or otherwise affect transmission of energy to or from the electrode.

Figure 22:
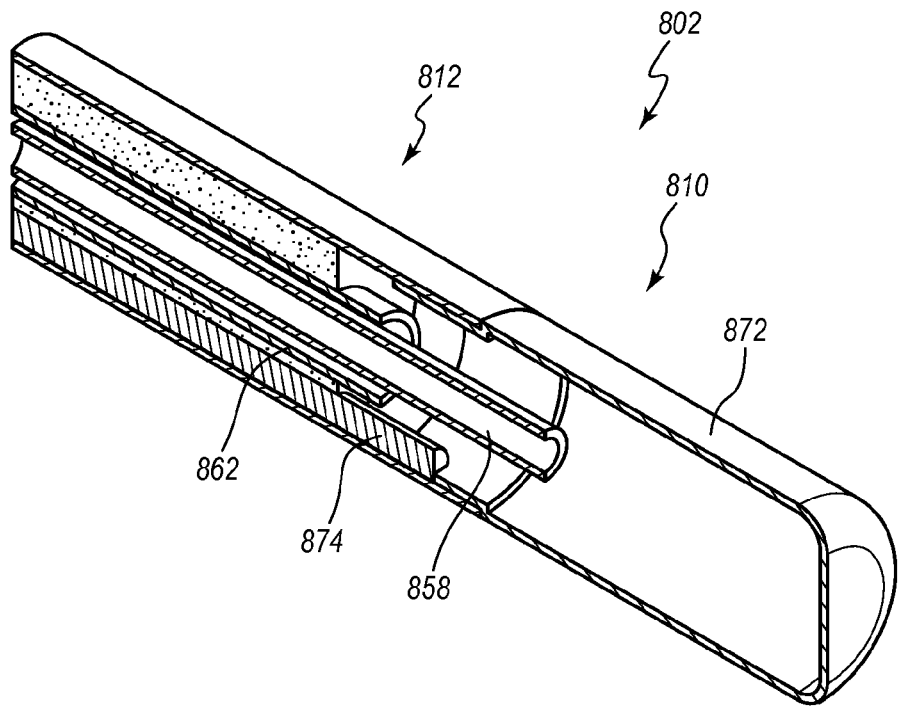
FIG. 22 is a cross-sectional perspective view of another embodiment of an electrode assembly.

FIG. 22 depicts a distal end of another embodiment of a leading assembly 802 that is similar to the leading assembly 702 discussed above. The leading assembly 802 includes a magnetic electrode assembly 810 and an intracorporeal positioning device 812 attached thereto. The magnetic electrode assembly 810 can resemble the magnetic electrode assembly 710 in many respects. However, the assembly 810 can be devoid of an internal magnetic member. Instead, the magnetic electrode assembly 810 includes an electrode 872 that is also a magnetic member. Stated otherwise, the magnetic member of the electrode 872 can include an electrode surface, which can be used in receiving or delivering electrical signals. In some embodiments, the electrode 872 comprises a magnetic source (e.g., a permanent magnet), whereas in other embodiments, the electrode comprises a magnetically influenced material that is unmagnetized. In the illustrated embodiment, the electrode 872 defines a thin wall so as to have a large surface area that can be readily cooled by a cooling medium. However, the volume of the magnetically influenced material that is present in the electrode 872 can be sufficient for a magnetic member in a complementary magnetic electrode assembly (e.g., the magnetic member 780 of the magnetic electrode assembly 720 in FIG. 20) to be attracted thereto with sufficient force for tracking. Other configurations are also possible.

The intracorporeal positioning device 812 includes an electrical lead 874 that is electrically coupled with the electrode 872. The intracorporeal positioning device 812 further includes fluid conduits 858, 862, such as the fluid conduits 758, 762 described above, for channeling a cooling medium both to and from the electrode 872.

Figure 23:
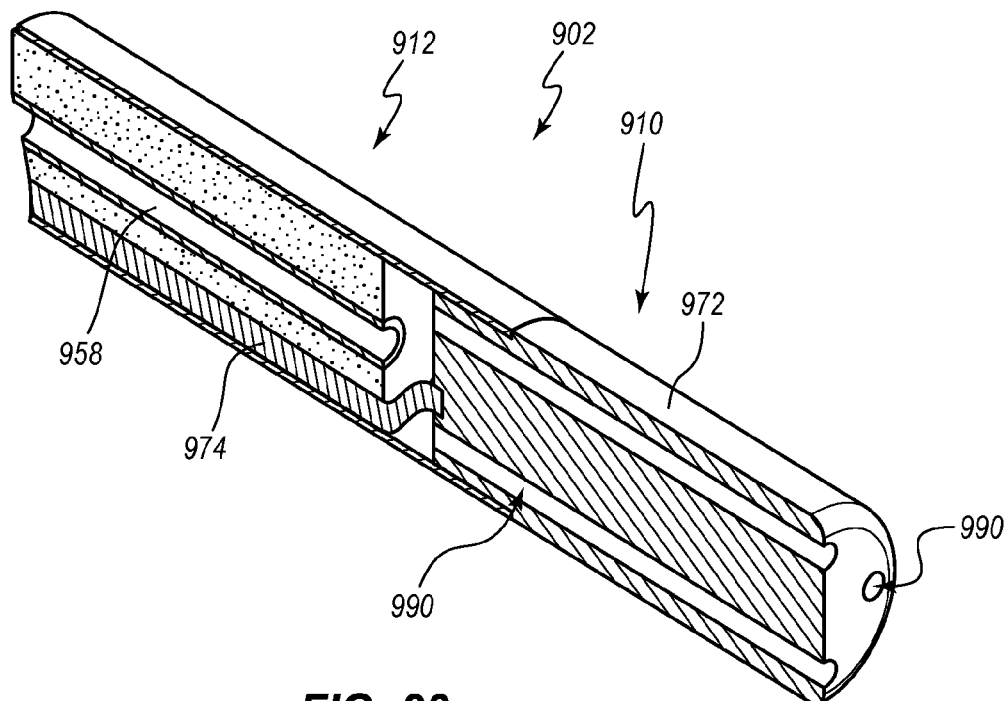
FIG. 23 is a cross-sectional perspective view of another embodiment of an electrode assembly.

FIG. 23 depicts a distal end of another embodiment of a leading assembly 902 that is similar to the leading assemblies 702, 802 discussed above. The leading assembly 902 includes a magnetic electrode assembly 910 and an intracorporeal positioning device 912 attached thereto. The magnetic electrode assembly 910 can resemble the magnetic electrode assemblies 710, 810 in many respects. However, unlike the electrode assembly 710, the assembly 910 can be devoid of a separate magnetic member, and unlike the electrode assembly 810, the assembly 910 can be configured to deliver cooling medium into the patient, rather than cycling the cooling fluid to a discharge unit at an exterior of the patient. The magnetic electrode assembly 910 includes an electrode 972 that is also a magnetic member. In some embodiments, the electrode 972 comprises a magnetic source (e.g., a permanent magnet), whereas in other embodiments, the electrode comprises a magnetically influenced material that is unmagnetized. In the illustrated embodiment, the electrode 972 defines a plurality of channels or ports 990 through which a cooling medium can pass so as to cool the electrode 972. The illustrated ports 990 are arranged substantially parallel to each other and are substantially parallel to a longitudinal axis of the electrode 972. Other configurations are also possible.

The intracorporeal positioning device 912 includes an electrical lead 974 that is electrically coupled with the electrode 972. The intracorporeal positioning device 912 further includes a fluid conduit 958 such as the fluid conduits 758, 858 described above, for channeling a cooling medium to the electrode 972.

Figure 24:
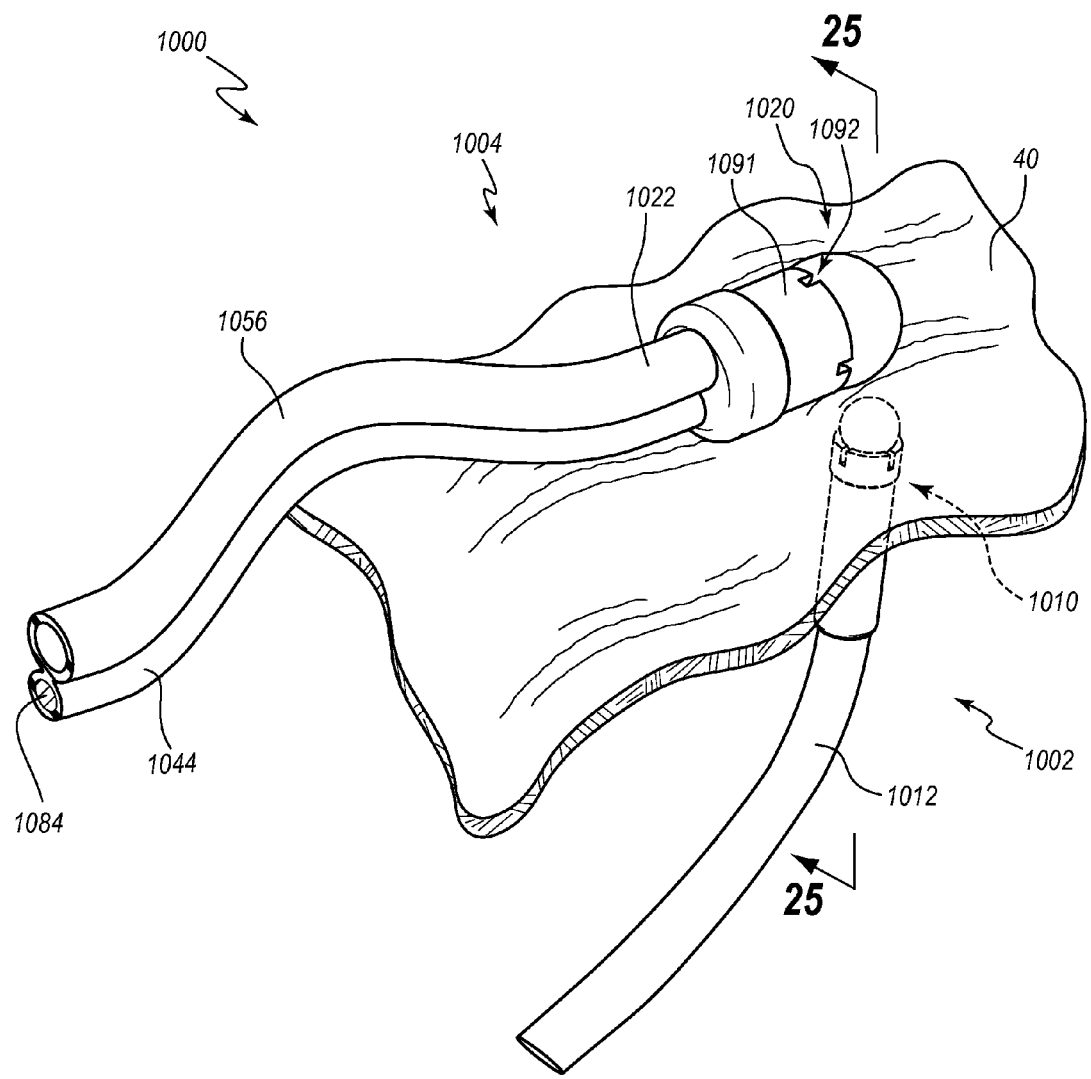
FIG. 24 is a perspective view of a distal portion of another embodiment of a magnetic coupling system that is shown coupled across an atrial wall.
Figure 25:
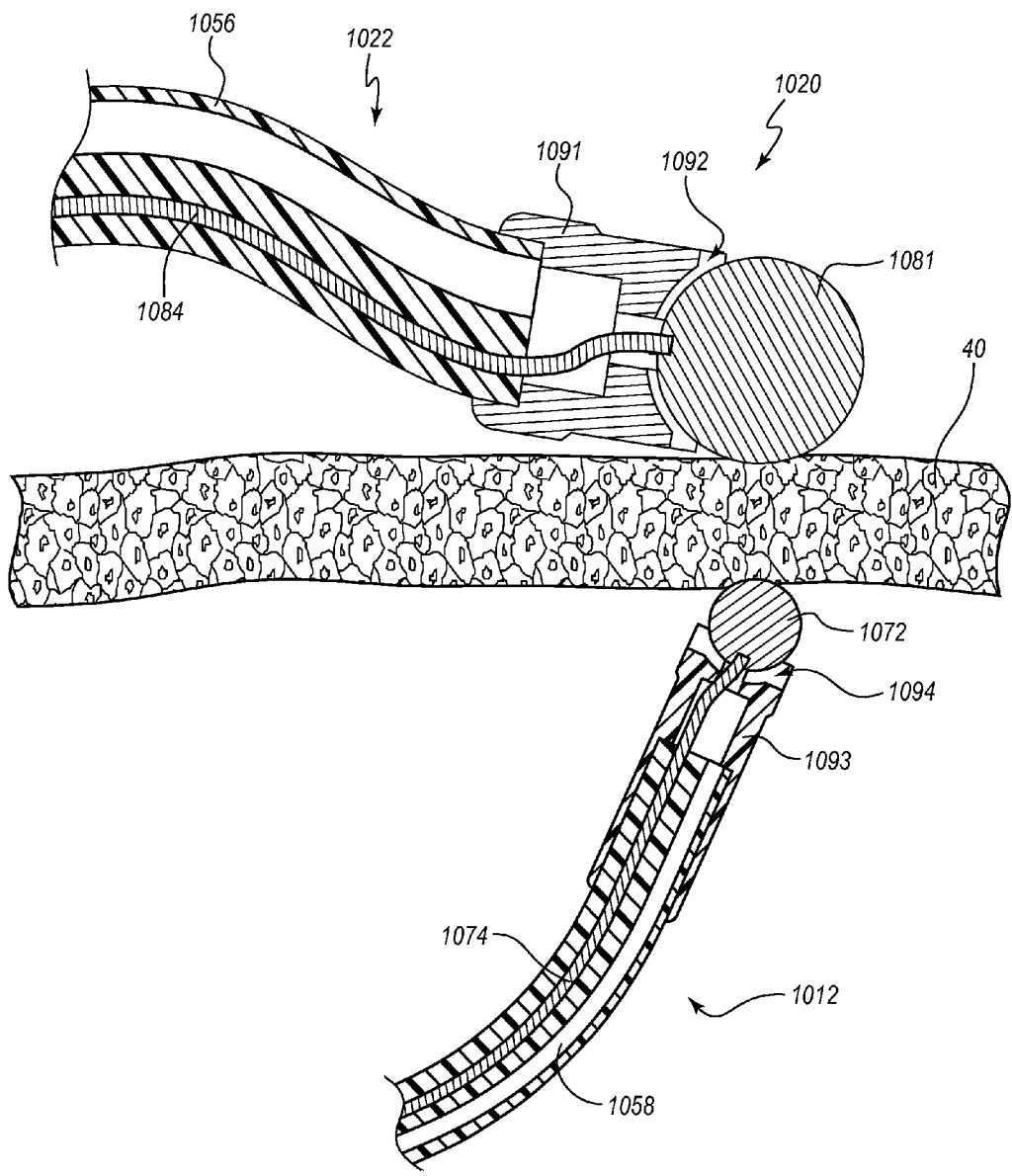
FIG. 25 is a cross-sectional view of the portion of the system shown in FIG. 24, taken along the view line 25-25.

FIGS. 24 and 25 depicts a distal end of another embodiment of a magnetic coupling system 1000 that is similar to the system 700 discussed above. The coupling system includes a leading assembly 1002 and a tracking assembly 1004 similar to the assemblies 702, 704.

The leading assembly 1002 includes a magnetic electrode assembly 1010 and an intracorporeal positioning device 1012 attached thereto. Any suitable attachment mechanism is possible. In the illustrated embodiment, the electrode assembly 1010 includes a collar 1093 that is fixedly secured to the positioning device 1012. The positioning device 1012 can comprise a steering catheter, such as describe above, or any other suitable configuration.

As with the electrode assembly 910 discussed above, the electrode assembly 1010 can be devoid of a separate magnetic member, and can be configured to deliver cooling medium into the patient, rather than cycling the cooling fluid to a discharge unit at an exterior of the patient. The magnetic electrode assembly 1010 includes an electrode 1072 that is also a magnetic member. In some embodiments, the electrode 1072 comprises a magnetic source (e.g., a permanent magnet), whereas in other embodiments, the electrode comprises a magnetically influenced material that is unmagnetized. The illustrated electrode 1072 is substantially spherical. In some embodiments, a spherically shaped electrode 1072, or an electrode that includes a rounded or curved end may be desirable. Such an arrangement may permit a concentrated or focused current between the electrode 1072 and an electrode 1081 of the tracking assembly 1004. Additionally, such the concentrated or focused current may be possible for a variety of orientations of the electrode assembly 1010; for example, the shape of a portion of the electrode 1072 that is closest to the atrial wall 40 when the positioning device 1012 is in the orientation shown in FIG. 25 may be substantially the same as the shape of another portion of the electrode 1072 that is closest to the atrial wall 40 when the positioning device 1012 defines a lower profile relative thereto (e.g., extends substantially parallel to the wall 40).

In the illustrated embodiment, the collar 1093 defines a plurality of channels or ports 1094 through which a cooling medium can pass so as to cool the electrode 1072. The illustrated ports 1094 extend along a base region of the electrode 1072.

The intracorporeal positioning device 1012 includes an electrical lead 1074 that is electrically coupled with the electrode 1072. The intracorporeal positioning device 1012 further includes a fluid conduit 1058 for channeling a cooling medium to the electrode 1072.

The tracking assembly 1004 includes a magnetic electrode assembly 1020 and an intracorporeal positioning device 1022 attached thereto. Any suitable attachment mechanism is possible. In the illustrated embodiment, the electrode assembly 1020 includes a collar 1091 that is fixedly secured to the positioning device 1022. The positioning device 1022 can comprise a percutaneous catheter or any other suitable configuration.

As with the electrode assembly 1010, the electrode assembly 1020 can be devoid of a separate magnetic member, and can be configured to deliver cooling medium into the patient, rather than cycling the cooling fluid to a discharge unit at an exterior of the patient. The magnetic electrode assembly 1020 includes an electrode 1081 that is also a magnetic member. In the illustrated embodiment, the electrode 1081 includes a magnetic source (e.g., a permanent magnet). It can be desirable for either one or both of the electrodes 1072, 1081 to comprise a magnetic source so as to be able to attract the other electrode. Where one electrode 1072, 1081 comprises a magnetic source, the other electrode 1072, 1081 may comprise a magnetically influenced material that is merely attracted to the magnetic source.

In other embodiments, each electrode 1072, 1081 may comprise a magnetic source, and thus the electrodes 1072, 1081 may have a preferential orientation relative to one another so that the electrodes 1072, 1081 can be attracted to each other. In certain of such embodiments, the electrodes 1072, 1081 are fixed relative to the collars 1093, 1091, respectively. In further embodiments, the collars 1093, 1091 do not exhibit any rotational freedom relative to the positioning devices 1012, 1022, and thus the positioning devices 1012, 1022 may likewise have a preferred orientation relative to each other, whereas in other embodiments, one or more of the collars 1091, 1012 may provide one or more degrees of rotational freedom. For example, in some embodiments, the electrodes 1072, 1081 may be capable of rotating within or relative to the collars 1093, 1091.

The illustrated electrode 1081 is substantially spherical. The spherical shape may permit the electrode 1081 to readily navigate about physiological features as it tracks the electrode 1072. Likewise, previously discussed, such an arrangement may permit a concentrated or focused current between the electrodes 1072, 1081. Additionally, such the concentrated or focused current may be possible for a variety of orientations of the electrode assembly 1020.

In the illustrated embodiment, the collar 1091 defines a plurality of channels or ports 1092 through which a cooling medium can pass so as to cool the electrode 1081. The illustrated ports 1092 extend along a base region of the electrode 1081.

The intracorporeal positioning device 1022 includes an electrical lead 1084 that is electrically coupled with the electrode 1081. The intracorporeal positioning device 1022 further includes a fluid conduit 1056 for channeling a cooling medium to the electrode 1081.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially cylindrical" is recited with respect to a feature, it is understood that in further embodiments, the feature can have a precisely cylindrical orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 ¶ 6. Embodiments of the invention in which an exclusive property or privilege is claimed are defined as follows.

The invention claimed is:

1. A system for heat ablation of a tissue wall of a patient, the system comprising:
   a first assembly configured to be positioned at a first side of the tissue wall, wherein the first assembly comprises:
      a first magnetic member comprising a magnetic source that provides a first magnetic field;
      a first electrode surface; and
      a first electrical lead electrically coupled with the first electrode surface so as to be capable of communicating electrical signals thereto; and
   a second assembly configured to be positioned at a second side of the tissue wall opposite the first side of the tissue wall, wherein the second assembly comprises:
      a second magnetic member configured to magnetically interact with the first magnetic field so as to be attracted to the first magnetic member;
      a second electrode surface; and
      a second electrical lead electrically coupled with the second electrode surface so as to be capable of communicating electrical signals thereto,
   wherein each of the first and second electrode surfaces are positioned relative to the first and second assemblies so as to contact the first and second sides of the tissue wall, respectively, due to the magnetic interaction of the second magnetic member with the first magnetic field,
   wherein one of the first and second assemblies is a leading assembly and the other of the first and second assemblies is a tracking assembly,
   wherein the leading assembly comprises an elongated positioning device that comprises a proximal portion that can be manipulated at an exterior of the patient to control movement of the magnetic member and the electrode surface of the leading assembly in any direction along a surface of the tissue wall, wherein the elongated positioning device comprises a rigid catheter, and
   wherein the tracking assembly is configured to dynamically track a position of the leading assembly as the leading assembly is moved via the positioning device in any direction along the surface of the tissue wall to maintain contact between the first electrode surface and the first side of the tissue wall and to maintain contact between the second electrode surface and the second side of the tissue wall, due to the magnetic interaction of the second magnetic member with the first magnetic field, as the first and second assemblies move relative to the tissue wall.

2. The system of claim 1, wherein a first electrode that is separate from the first magnetic member comprises the first electrode surface.

3. The system of claim 2, wherein the first electrode is electrically insulated from the first magnetic member.

4. The system of claim 1, wherein the first magnetic member comprises the first electrode surface such that electrical signals can be communicated through the magnetic member to the first electrode surface.

5. The system of claim 4, wherein the first electrical lead is electrically coupled with the first magnetic member.

6. The system of claim 1, wherein the first magnetic member is rotatable relative to the first electrode surface.

7. The system of claim 1, wherein the second magnetic member comprises one or more of a magnetic source that provides a second magnetic field configured to magnetically interact with the first magnetic member and a magnetically interactive material that does not provide a magnetic field.

8. The system of claim 1, wherein the elongated positioning device of the leading assembly contains at least a portion of one of the first and second electrical leads therein.

9. The system of claim 1, wherein the elongated positioning device comprises a steering catheter having a remotely positionable distal end.

10. The system of claim 9, wherein the tracking assembly comprises a linkage that is sufficiently flexibly to permit the electrode surface of the tracking assembly to maintain dynamic alignment with the electrode surface of the leading assembly as the leading and tracking assemblies are moved relative to the tissue wall in any direction.

11. The system of claim 1, wherein the elongated positioning device further comprises a fluid conduit through which a cooling medium can be channeled.

12. The system of claim 1, wherein the first and second electrical leads are coupled with a radiofrequency generator that is configured to generate a radiofrequency signal that is communicated through the tissue wall.

13. The system of claim 1, wherein the first and second electrical leads are coupled with a control system that is configured to electrically map the tissue wall based on signals measured via one of more of the first and second electrode surfaces.

14. The system of claim 13, wherein the control system is configured to determine a voltage difference between the first and second electrode surfaces so as to monitor electrical properties of the mid-myocardium.

15. The system of claim 1, wherein the first and second electrical leads are coupled with a control system that is configured to monitor an electrical conductance between the first and second electrodes during an ablation procedure and to adjust an amount of ablation energy delivered to the first and second electrodes in response to a measured level of the electrical conductance.

16. The system of claim 1, wherein the tracking assembly is configured to track a position of the leading assembly to maintain contact between the first electrode surface and the first side of the tissue wall and to maintain contact between the second electrode surface and the second side of the tissue wall as the tissue wall is ablated via the first and second electrode surfaces while the electrode surfaces move relative to the tissue wall.

17. The system of claim 1, wherein the tracking assembly comprises a linkage that is sufficiently flexible to maintain dynamic alignment of the first and second electrode surfaces as the first and second assemblies move relative to the tissue wall in any direction.

18. The system of claim 17, wherein the magnetic member of the leading assembly defines a channel at an interior of the magnetic member through which a cooling medium can flow.

19. The system of claim 18, wherein the magnetic member of the leading assembly is configured to contact the cooling medium only at an interior surface of the magnetic member and is configured to prevent the cooling medium from coming into contact with the tissue wall.

20. The system of claim 18, wherein the channel extends through an end of the magnetic member of the leading assembly to permit the cooling medium to be delivered into contact with the tissue wall at an exterior of the magnetic member.

21. The system of claim 18, further comprising an electrode that defines the electrode surface of the leading assembly, wherein the electrode cooperates with the magnetic member of the leading assembly to define a channel at an exterior of the magnetic member through which a cooling medium can flow.

22. The system of claim 21, wherein the electrode is configured to contact the cooling medium only at an interior surface of the electrode.

23. A method for heat ablation of a tissue wall, the method comprising:
   positioning a first assembly at a first side of the tissue wall, wherein the first assembly comprises:
      a first magnetic member comprising a magnetic source that provides a magnetic field;
      a first electrode surface; and
      a first electrical lead electrically coupled with the first electrode surface so as to communicate electrical signals thereto;
   positioning a second assembly at a second side of the tissue wall opposite the first side of the tissue wall, wherein the second assembly comprises:
      a second magnetic member that magnetically interacts with the magnetic field so as to be magnetically coupled with the first magnetic member;
      a second electrode surface; and
      a second electrical lead electrically coupled with the second electrode surface so as to communicate electrical signals thereto,
   wherein one of the first and second assemblies is a leading assembly and the other of the first and second assemblies is a tracking assembly, and wherein the leading assembly comprises an elongated positioning device that comprises a proximal portion, and wherein the elongated positioning device comprises a rigid catheter;
   contacting the first and second electrode surfaces to the first and second sides of the tissue wall, respectively;
   communicating electrical energy through the tissue wall via the first and second electrode surfaces to ablate the tissue wall; and manipulating the proximal portion of the positioning device at a position exterior to the patient to reposition the first electrode surface in any direction relative to the tissue wall while the first and second magnetic members are magnetically coupled with each other and while electrical energy is being communicated through the tissue wall via the first and second electrode surfaces,
   wherein the tracking assembly dynamically tracks a position of the leading assembly to maintain contact between the first electrode surface and the first side of the tissue wall and to maintain contact between the second electrode surface and the second side of the tissue wall, due to the magnetic interaction of the second magnetic member with the first magnetic field, as the first and second assemblies move relative to the tissue wall.

24. The method of claim 23, wherein the elongated positioning device comprises a steering catheter, and wherein said repositioning the first electrode surface automatically causes the second electrode surface to be repositioned so as to remain aligned with the first electrode surface.

25. The method of claim 23, wherein the magnetic field is sufficiently strong to maintain the second electrode surface in contact with the tissue wall while electrical energy is communicated via the first and second electrode surfaces without clamping the first and second assemblies to the tissue wall.

26. The method of claim 23, further comprising:
   monitoring an electrical conductance between the first and second electrodes while electrical energy is communicated through the tissue wall; and
   adjusting an amount of ablation energy delivered to the first and second electrodes in response to a measured level of the electrical conductance.

27. A system for heat ablation of a tissue wall of a patient, the system comprising:
   a first assembly configured to be positioned at a first side of the tissue wall, wherein the first assembly comprises:
      a first magnetic member comprising a magnetic source that provides a first magnetic field;
      a first electrical lead electrically coupled with the first magnetic member so as to be capable of communicating electrical signals thereto; and a second assembly configured to be positioned at a second side of the tissue wall opposite the first side of the tissue wall, wherein the second assembly comprises:
- a second magnetic member configured to magnetically interact with the first magnetic field so as to be attracted to the first magnetic member; and
- a second electrical lead electrically coupled with the second magnetic member so as to be capable of communicating electrical signals thereto, wherein each of the first and second magnetic members are positioned relative to the first and second assemblies so as to contact the first and second sides of the tissue wall, respectively, due to the magnetic interaction of the second magnetic member with the first magnetic field, wherein one of the first and second assemblies is a leading assembly and the other of the first and second assemblies is a tracking assembly, wherein the leading assembly comprises an elongated positioning device that comprises a proximal portion that can be manipulated at an exterior of the patient to control movement of the magnetic member of the leading assembly in any direction along a surface of the tissue wall, wherein the elongated positioning device comprises a rigid catheter, and wherein the tracking assembly is configured to dynamically track a position of the leading assembly as the leading assembly is moved via the positioning device in any direction along the surface of the tissue wall to maintain contact between the first electrode surface and the first side of the tissue wall and to maintain contact between the second electrode surface and the second side of the tissue wall, due to the magnetic interaction of the second magnetic member with the first magnetic field, as the first and second assemblies move relative to the tissue wall.

28. The system of claim 27, wherein the tracking assembly is configured to track a position of the leading assembly to maintain contact between the first electrode surface and the first side of the tissue wall and to maintain contact between the second electrode surface and the second side of the tissue wall as the tissue wall is ablated via the first and second electrode surfaces while the electrode surfaces move relative to the tissue wall.

29. The system of claim 27, wherein the elongated positioning device comprises a steering catheter having a remotely positionable distal end.

30. The system of claim 27, wherein the magnetic member of the leading assembly defines a channel at an interior of the magnetic member through which a cooling medium can flow.

31. The system of claim 30, wherein the magnetic member of the leading assembly is configured to contact the cooling medium only at an interior surface of the magnetic member.

32. The system of claim 30, wherein the channel extends through an end of the magnetic member of the leading assembly to permit the cooling medium to be delivered into contact with the tissue wall at an exterior of the magnetic member.

* * * * *